United States Patent
Pfleger et al.

(10) Patent No.: US 10,525,038 B2
(45) Date of Patent: **\*Jan. 7, 2020**

(54) COMBINATION THERAPY

(71) Applicant: DIMERIX BIOSCIENCE PTY LTD, Nedlands, Western Australia (AU)

(72) Inventors: Kevin D. G. Pfleger, Nedlands (AU); Elizabeth McCall, Dalkeith (AU); James Williams, Kensington (AU)

(73) Assignee: DIMERIX BIOSCIENCE PTY LTD., Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/704,713

(22) Filed: Sep. 14, 2017

(65) Prior Publication Data

US 2018/0000826 A1    Jan. 4, 2018

Related U.S. Application Data

(60) Continuation of application No. 15/086,823, filed on Mar. 31, 2016, which is a division of application No. 13/979,127, filed as application No. PCT/AU2012/000014 on Jan. 11, 2012, now Pat. No. 9,314,450.

(60) Provisional application No. 61/432,896, filed on Jan. 14, 2011, provisional application No. 61/547,951, filed on Oct. 17, 2011.

(30) Foreign Application Priority Data

Jan. 11, 2011 (AU) .............................. 2011900060
Oct. 17, 2011 (AU) .............................. 2011904279

(51) Int. Cl.
| | | |
|---|---|---|
| A61K 31/537 | (2006.01) | |
| A61K 9/00 | (2006.01) | |
| A61K 9/20 | (2006.01) | |
| A61K 31/28 | (2006.01) | |
| A61K 31/4178 | (2006.01) | |
| A61K 31/4184 | (2006.01) | |
| A61K 31/80 | (2006.01) | |
| A61K 45/06 | (2006.01) | |

(52) U.S. Cl.
CPC ........ *A61K 31/4184* (2013.01); *A61K 9/0019* (2013.01); *A61K 9/2009* (2013.01); *A61K 9/2054* (2013.01); *A61K 31/28* (2013.01); *A61K 31/4178* (2013.01); *A61K 31/537* (2013.01); *A61K 31/80* (2013.01); *A61K 45/06* (2013.01)

(58) Field of Classification Search
CPC .. A61K 31/537; A61K 9/0019; A61K 9/2009; A61K 9/2054; A61K 31/28; A61K 31/4178; A61K 31/4184; A61K 31/80; A61K 45/06
See application file for complete search history.

(56) References Cited

U.S. PATENT DOCUMENTS

| | | |
|---|---|---|
| 4,391,904 A | 7/1983 | Litman et al. |
| 4,671,958 A | 6/1987 | Rodwell et al. |
| 4,751,180 A | 6/1988 | Cousens et al. |
| 4,925,673 A | 5/1990 | Steiner et al. |
| 4,935,233 A | 6/1990 | Bell et al. |
| 5,013,556 A | 5/1991 | Woodle et al. |

(Continued)

FOREIGN PATENT DOCUMENTS

| | | |
|---|---|---|
| EP | 0521680 A1 | 1/1993 |
| EP | 1 422 228 | 5/2004 |

(Continued)

OTHER PUBLICATIONS

Chouliaras et al (Year: 2010).*

(Continued)

*Primary Examiner* — Rachael E Bredefeld
*Assistant Examiner* — Ibrahim D Bori
(74) *Attorney, Agent, or Firm* — MH2 Technology Law Group, LLP

(57) ABSTRACT

The invention relates to pharmaceutical compositions comprising: (a) at least one angiotensin receptor blocker or a pharmaceutically acceptable salt thereof, and (b) at least one chemokine receptor pathway inhibitor or a pharmaceutically acceptable salt thereof. The invention also relates to pharmaceutical compositions comprising: (a) at least one angiotensin receptor blocker or a pharmaceutically acceptable salt thereof; and (b) at least one chemokine receptor pathway inhibitor or a pharmaceutically acceptable salt thereof which inhibits a component of the chemokine receptor pathway other than the chemokine receptor. Oral sustained release pharmaceutical compositions comprising the pharmaceutical composition, as well as injectable sustained release pharmaceutical compositions comprising the pharmaceutical composition are described. The invention further relates to tablets, capsules, injectable suspensions, and compositions for pulmonary or nasal delivery comprising the pharmaceutical composition. Also described are: methods for assessing the efficacy of the pharmaceutical composition; methods for assessing the inhibition or partial inhibition activity of the pharmaceutical composition; methods for the treatment, amelioration or prevention of a condition or disease comprising administering to a subject a therapeutically effective amount of the pharmaceutical composition; and the use of the pharmaceutical composition for the manufacture of a dosage form for the treatment of a disease.

22 Claims, 9 Drawing Sheets

(56) References Cited

U.S. PATENT DOCUMENTS

| | | | |
|---|---|---|---|
| 5,492,904 | A | 2/1996 | Wong |
| 5,663,188 | A | 9/1997 | Fossa et al. |
| 5,891,646 | A | 4/1999 | Barak et al. |
| 6,110,693 | A | 8/2000 | Barak et al. |
| 6,800,445 | B2 | 10/2004 | Palmer et al. |
| 6,893,827 | B1 | 5/2005 | Palmer et al. |
| 7,049,076 | B2 | 5/2006 | Lee et al. |

FOREIGN PATENT DOCUMENTS

| | | |
|---|---|---|
| JP | 5-9116 | 1/1993 |
| JP | 2005-528721 | 9/2002 |
| JP | 2004-093527 | 3/2004 |
| JP | 2010-540527 A | 12/2010 |
| WO | 96/40258 | 12/1996 |
| WO | WO 00/25134 | 5/2000 |
| WO | WO 04/022786 | 3/2004 |
| WO | WO 05/050182 | 4/2005 |
| WO | WO 05/031309 | 6/2005 |
| WO | 2006/029349 | 3/2006 |
| WO | 2006/000421 | 1/2008 |
| WO | 2008/055313 | 5/2008 |
| WO | 2008/060621 | 5/2008 |
| WO | WO 08/056313 | 5/2008 |
| WO | 2008/113095 | 9/2008 |
| WO | 2009/042193 | 4/2009 |
| WO | 2009/042193 A1 | 4/2009 |
| WO | 2009/073683 | 6/2009 |
| WO | 2009/125168 | 10/2009 |
| WO | 2010/065069 | 6/2010 |
| WO | 2010/108232 | 9/2010 |

OTHER PUBLICATIONS

Urushihara et al (Year: 2010).*
Atkins et al (Year: 2005).*
Kanamori et al (Year: 2007).*
Urushihara (Year: 2010).*
Supplementary European Search Report dated May 16, 2014 from European Patent Application No. 12 73 4251, pp. 1-6.
Ihm, Chun-Gyoo et al. Effects of therapeutic agents on the inflammatory and fibrogenic factors in iGA nephropathy, Nephrology, Dec. 1, 2007, vol. 12, No. 13, pp. S25-S26.
Zhang, Yan et al., Effects of mycophenolate mofetil, valsartan and their combined therapy on preventing pedocyte loss in early stage of diabetic nephropathy in rats. Chinese Medical Journal, Jun. 1, 2007, vol. 120, No. 11, pp. 988-995.
Lin, Shuei-Liong et al. Effect of Pentoxifylline in Addition to Losartan on Proteinuria and GFR in CKD: A 12-Month Randomized Trial. American Journal of Kidney Diseases, Sep. 1, 2008, vol. 52, No. 3, pp. 464-474.
Naito, Masayo et al. High Ambient Glucose Augments Angiotensin II-Induced Proinflammatory Gene mRNA Expression in Human Mesangial Cells: Effects of Valsartan and Simvastatin, American Journal of Nephrology, Jan. 1, 2009, vol. 30, No. 2, pp. 99-111.
Major, Terry C. et al. A CCR2/CCR5 Antagonist Attenuates an Increase in Angiotensin II-Induced CD11b+ Monocytes from Atherogenic ApoE-/-Mice, Cardiovascular Drugs and Therapy, Dec. 4, 2008, vol. 23, No. 2, pp. 113-120.
Struthers, Mary et al. CCR2 Antagonists. Current Topics in Medicinal Chemistry, Jan. 1, 2010, vol. 10, No. 13, pp. 1278-1298.
Xia, Mingde et al. Recent developments in CCR2 antagonists. Expert Opinion on Therapeutic Patents, Mar. 1, 2009, vol. 19, No. 3, pp. 295-303.
Dai, Q. et al. Angiotensin AT1 receptor antagonists exert anti-inflammatory effects in spontaneously hypertensive rats. British Journal of Pharmacology, Dec. 29, 2007, vol. 157, No. 7, pp. 1042-1048.
Kanamori, Hiroshi et al. Inhibition of MCP-1/CCR2 pathway ameliorates the development of diabetic nephropathy ScienceDirect, Sep. 2, 2007, vol. 360, No. 4, pp. 772-777.
Cho, Byoung-Soo et al. Effects of Bupleurum falcatum and its Combination with an Angiotensin II Receptor Blocker on Cytokine and Chemokine Expression in Human Mesangial Cells, Phytotherapy Research, Mar. 1, 2010, vol. 24, No. 3, pp. 339-343.
Okada, Takuya et al., Combined Treatment with Valsartan and Spironolactone Prevents Cardiovascular Remodelling in Renovascular Hypertensive Rats, International Heart Journal, Sep. 2006, vol. 47, No. 5, pp. 783-793.
Urushihara, Maki et al. Addition of Anglotensin II Type 1 Receptor Blocker to CCR2 Antagonists Markedly Attenuates Crascentic Glomerulonaphritis. Hypertension, Mar. 2011, pp. 586-593.
Nabah, Yafa Naim Abu et al. CXCR2 Blockade Impairs Angiotensin II-Induced CC Chemokine Synthesis and Mononuclear Leukoncyte infiltration. Arteriosclerosis, Thrombosis, and Vascular Biology, Nov. 11, 2007, pp. 2370-2376.
Tsukuda, Kana et al. Irbesartan attenuates ischemic brain damage by inhibition of MCP-1/CCR2 signaling pathway beyond AT1 receptor blockade. Biochemical and Biophysicl Research Communications, Jun. 3, 2011, pp. 275-279.
AbdAlla, Said et al. AT1-receptor heterodimers show enhanced G-protein activation and altered receptor sequestration. Letters to Nature, Sep. 7, 2000, vol. 407, pp. 94-98.
AbdAlla, Said et al. Increased AT1 receptor heterodimers in preeclampsia mediate enhanced angiotensin II responsiveness. Nature Medicine, Sep. 2001, vol. 7, No. 9, pp. 1003-1009.
Adams, Stephen R. et al. New Blarsenical Ligands and Tetracysteine Motifs for Protein Labeling in Vitro and in Vivo: Synthesis and Biological Applications, JACS Articles, American Chemical Society, Dec. 5, 2001, Issue 124, pp. 6063-6076.
Agnati, LF et al. Existence and theoretical aspects of homomeric and heromeric dopamine receptor complexes and their relevance for neurological disease. Neuromolecular Med, 2005;7(1-2):61-78.
Angers, S. et al. Biochemical and biophysical demonstration of GPCR oligomerization in mammalian cells. Life Sciences 68 (2001) 2243-2250.
Angers, Stephane et al. Detection of b2-adrenergic receptor dimerization in living cells using bioluminescance resonance energy transfer (BRET). PNAS, Mar. 28, 2000, vol. 97, No. 7, pp. 3684-3689.
Auerbach, Daniel et al. The post-genomic era of interactive proteomics: Facts and perspectives. Proteomics, 2002, 2, 611-623.
Ayoub, Mohammed A. et al. Monitoring of Ligand-independant Dimerization and Ligand-induced Conformational Changes of Melatonin Receptors in Living Cells by Bioluminescence Resonance Energy Transfer. The Journal of Biological Chemistry, Jun. 14, 2002, vol. 277, No. 24, pp. 21522-21528.
Ayoub, Mohammed A. et al. Preferential Formation of MT1/MT2 Melatonin Receptor Heterodimers with Distinct Ligand Interaction Properties Compared with MT2 Homodimers. Molecular Pharmacology, 2004, vol. 66, No. 2 398/1166334, p. 312-321.
Babcock, Gregory J. et al. Ligand-independent Dimerization of CXCR4, a Principal HIV-1 Coreceptor. The Journal of Biological Chemistry, 2003, vol. 278, No. 5, Issue of Jan. 31, pp. 3378-3385.
Bai, Mei. Structure-funtion relationship of the extracellular calcium-sensing receptor. Cell Calcium 35 (2004) 197-207.
Baumann, Christian R. et al. Hypocretins (orexins): clinical impact of the discovery of a neurotransmitter. Sleep Medicine Reviews (2005) 9, 253-268.
Berglund, Magnus M. et al. Neuropeptide Y Y4 Receptor Homodimers Dissociate upon Agonist Stimulation, The Journal of Pharmacology and Experimental Therapeutics, vol. 307, No. 3, JPET 307:1120-1126, 2003.
Berthouze, Magali et al. Constitutive dimerization of human serotonin 5-HT4 receptors in living cells. FEBS Letters 579 (2005) 2973-2980.
Bouvier, Michel. "Oligomerization of G-Protein-Coupled Transmitter Receptors". REviews. Mcmilliam Magazines Ltd. Apr. 2001, vol. 2. pp. 274-286.
Breit, Andress et al. "Hatero-oligomerization between b2- and b3-Adrenergic Receptors Generates a b-Adrenergic Signaling Unit with Distinct Functional Properties". The Journal of Biological Chemistry. vol. 279, No. 27, Issue of Jul. 2, pp. 28756-28765, 2004.
Breit, Andreas et al. "Simultaneous Activation of the delta Optoid Receptor (delta OR)/Sensory Neuron-Specific Receptor-4 (SNSR-

(56) References Cited

OTHER PUBLICATIONS

4) Hetero-Oligomer by the Mixed Bivalent Agonist Bovine Adrenal Madulla Peptide 22 Activates SNSR-4 but Inhibits delta or Signaling". Molecular Pharmacology, vol. 70, No. 2, Mol Pharmacol 70:686-696, 2006.
Breitwieser, Gerda E. "G Protein-Coupled Receptor Oligomerization: Implications for G Protein Activation and Cell Signaling". Circulation Research. 2004; 94; 17-27.
Brisbare-Roch, Catherine et al. "Promotion of sleep by targeting the orexin system in rats, dogs and humans". Nature Medicine. Feb. 2007, vol. 13, No. 2, pp. 150-155.
Bruchez, Marcel. "Semiconductor Nanocrystals as Fluorescent Biological Labels". Science 281, 2013 (1998); pp. 2013-2016.
Bulenger, Sebastien et al. "Emerging role of homo- and heterodimerization in G-Protein-coupled receptor biosynthesis and maturation", Trends in Pharmacological Sciences vol. 26 No. 3, Mar. 2005, pp. 131-137.
Cambell, Robert E. et al. "A monomeric red fluorescent protein", PNAS, Jun. 11, 2002. vol. 99, No. 12, 7877-7882.
Canals, Meritxell et el. "Adenosine A2A-Dopamine D2 Receptor-Receptor Heteromerization". The Journal of Biological Chemistry, vol. 278, No. 47, Issue of Nov. 21, pp. 46741-46749, 2003.
Carrillo, Juan J. "Dimers of Class A G Protein-coupled Receptors Function via Agonist-mediated Trans-activation of Associated G Proteins". The Journal of Biological Chemistry. vol. 278, No. 43, Issue of Oct. 24, pp. 42578-42587, 2003.
Chen, Chii-Heui et al. "Termination of Protease-activated Receptor-1 Signaling by b-Arrestins is Independent of Receptor Phosphorylation", The Journal of Biological Chemistry. vol. 279, No. 11, Issue of Mar. 12, pp. 10020-10031, 2004.
Cheng Zhi-Jie et al. "Agonist-depandent Dissociation of Oligomeric Complexes of G Protein-coupled Cholecystokinin Receptors Demonstrated in Living Cells Using Bioluminescence Resonance Energy Transfer". The Journal of Biological Chemistry. vol. 276, No. 51, Issue of Dec. 21, pp. 48040-48047, 2001.
Chinenov, Yurii. "Close encounters of many kinds: Fos-Jun interactions that mediate transcription specificity". Oncogene (2001) 20, 2438-2452.
Ciruela, Francisco. "Presynaptic Control of Striafal Glutamatergic Neurotransmission by Adenosins A1-A2A Receptor Heteromers". The Journal of Neuroscience, Feb. 15, 2006 • 26(7):2080-2087.
De, Abhijit. An Improved Bioluminescence Resonance Energy Transfer Strategy for Imaging Intracellular Events in Single Cells and Living Subjects. Cancer Res 2007;67:7175-7183, Published online Aug. 1, 2007.
de Wet, Jeffrey R. "Firefly Luciferase Gene; Structure and Expression in Mammalian Cells", Molecular and Cellular Biology, Feb. 1987, p. 725-737 vol. 7, No. 2.
Devost, "Homo- and Hetero-Dimeric Complex Formations of the Human Oxytocin Receptor", Journal of Neuroendocrinology, 2004, vol. 18, 372-377.
Eidne, Karin A. "Applications of novel resonance energy transfer techniques to study dynamic hormone receptor interactions in living cells". Trends in Endocrinology & Metabolism vol. 13 No. 10 Dec. 2002. pp. 415-421.
El-Asmar, Laila. "Evidence for Negative Binding Cooperativity within CCR5-CCR2b Heterodimers". Molecular Pharmacology. 67;460-469, 2005.
Ellis, James. "Orexin-1 Receptor-Cannabinold CB1 Receptor Heterodimerization Results in Both Ligand-dependent and -independent Coordinated Alterations of Receptor Receptor Localization and Functions", The Journal of Biological Chemistry, vol. 281, No. 50, pp. 38812-38824, Dec. 15, 2006.
Fradkov, Arkady F. "Far-red fluorescent tag for protein labelling". Biochem. J. (2002) 368, 17-21 (Printed in Great Britain).
Frank, Monika, "G Protein Activation without Subunit Dissociation Depends on a Gαi-specific Region", The Journal of Biological Chemistry. vol. 280, No. 26, Issue of Jul. 1, pp. 24584-24590, 2005.

Fuxe, K. "Adenosine A2A and dopamine D2 heteromeric receptor complexes and their function", J Mol Neurosci. 2005;26(2-3):209-20.
Gales, Celine, "Real-time monitoring of receptor and G-protein interactions in living cells", Nature Method, vol. 2, 3, Mar. 2005, pp. 177-184.
Gales, Celine, "Probing the activation-promoted structural rearrangements in preassembled receptor-G protein complexes", Nature Structural & Molecular Biology. vol. 13, No. 9. Sep. 2006, pp. 778-786.
Gary, Keith A. "The Thyrotropin-Releasing Hormone (TRH) Hypothesis of Homeostatic Regulation: Implications for TRH-Based Therapeutics", The Journal of Pharmacology and Experimental Therapeutics. vol. 305, No. 2, pp. 410-416.
George, Susan R. "G-Protein-Coupled Receptor Oligomerization and Its Potential for Drug Discovery", Nature. Oct. 2002. vol. 1. pp. 808-820.
Gomes, Ivone. "Oligomerization of oploid receptors". Methods 27 (2002) 358-365.
Gomes, Ivone. "A role for hetarodimerization of micor and delta Opiate receptors in enhancing morphine analgesia". PNAS. Apr. 6, 2004. vol. 101, No. 14, 5135-5139.
Grant, Michael "Agonist-depandant Dissociation of Human Somatostatin Receptor 2 Dimers", The Journal of Biological Chemistry, vol. 279, No. 35, Issue of Aug. 27, pp. 36179-36183, 2004.
Greer, Lee F. "Imagine of light emission from the expression of luciterases in living cells and orfanisms: a review", Luminescence 2002;17:43-74.
Gregan, Bernd, "Ligand-dependent Differences in the Internalization of Endothelin A and Endothelin B Recaptor Heterodimers", The Journal of Biological Chemistry, vol. 279, No. 26, Issue of Jun. 25, pp. 27679-27687, 2004.
Griffin, B. Albert. "Specific Covalent Labeling of Recombinant Protein Molecules Inside Live Cells". Science 281, 269 (1998), pp. 269-272.
Gupta, Achia. "Targeting Opiold Receptor Heterodimers: Strategies for Screening and Drug Development", The AAPS Journal 2006; 8 (1) Article 18. pp. 153-159.
Gurskaya, Nadya G. "GFP-like chromoproteins as a source of far-red fluorescent proteins", FEBS Letters 507 (2001) 16-20.
Hamden, Fedi F. "High-Throughput Screening of G Protein-Coupled Receptor Antagonists Using a Bioluminescence Resonance Energy Transfer 1-Based b-Arrestin2 Recruitment Assay", J Biomol Screen 2005 10: 463, pp. 463-475.
Hansen, Jakob. "Functional consequences of 7TM receptor dimerization", European Journal Pharmaceutical Sciences 23 (2004) 301-317.
Hansen, Jakob, "Oligomerization of Wild Type and Nonfunctional Mutant Angiotensin II Type I Receptors Inhibits Gq Protein Signaling but Not ERK Activation", The Journal of Biological Chemistry. vol. 279, No. 23, Issue of Jun. 4, pp. 24108-24115, 2004.
Hanyaloglu, Aylin C. "Homo- and Hetero-oligomerization of Thyrotropin-releasing Hormone (TRH) Receptor Subtypes". The Journal of Biological Chemistry. vol. 277, No. 52, Issue of Dec. 27, pp. 50422-50430, 2002.
Harikumar, Kaleeokal G. "Constitutive Formation of Oligomeric Complexes between Family B G Protein-Coupled Vasoactive Intestinal Polypeptide and Secretin Receptors", Molecular Pharmacology 69:363-373, 2006.
Harrison, Charlotte. "Current methods used to Investigate G protein coupled receptor oligomerisation", Journal of Pharmacological and Toxicological Methods 54 (2006) 26-35.
Hastings, J. Woodland. "Chemistries and colors of bioluminescent reactons: a review". Gene, 173 (1996) 5-11.
Haynes, Andrea C. "A selective orexin-1 receptor antagonist reduces food consumption in male and female rate", Regulatory Peptides 96 (2000) 45-51.
Hebert, Terence E. "Detecting and Imaging Protein-Protein Interactions During G Protein-Mediated Signal Transduction In Vivo and In Situ by Using Fluorescence-Based Techniques". Cell Chemistry and Biophysics. vol. 45, 2006, pp. 85-110.
Heding, Anders, "The Rat Gonadotropin-Releasing Hormone Receptor Internalizes via a ß-Arrestin-Independent, but Dynamin-

(56) References Cited

OTHER PUBLICATIONS

Dependent, Pathway: Addition of a Carboxyl-Terminal Tail Confers ß-Arrestin Dependency", Endocrinology 2000 141:299-306.
Helm Roger. "Wavelength mutations and posttranslational autoxidation of green fluorescent protein". Proc. Natl. Acad. Sai, USA, vol. 91, pp. 12501-12504, Dec. 1994.
Hernanz-Falcon, Patricia. "Identification of amino acid residues crucial for chemokine receptor dimerization", Nature Immunology. vol. 5, No. 2, Feb. 2004, pp. 216-223.
Herrick-Davis, Katharine, "Biochemical and Biophysical Characterization of Serotonin 5-HT2C Receptor Homodimers on the Plasma Membrane of Living Cells". Biochemistry 2004, 43, 13963-13971.
Herrick-Davis, Katharine. "Inhibition of Serotonin 5-Hydroxytryptamine2C Receptor Function through Heterodimerization". The Journal of Biological Chemistry. vol. 280, No. 48, pp. 40144-40151, Dec. 2, 2005.
Herrick-Davis, Katharine,"Serotonin 5-HT2C Receptor Homodimer Biogenesis in the Endoplasmic Reticulum", The Journal of Biological Chemistry, vol. 281, No. 37, pp. 27109-27116, Sep. 15, 2006.
Hilairet, Sandrine, "Hypersensitization of the Orexin 1 Receptor by the CB1 Rececptor", The Journal of Biological Chemistry, vol. 278, No. 26, Issue of Jun. 27, pp. 23731-23737, 2003.
Hirose, Masaaki, "N-Acyl 6,7-Dimethoxy-1,2,3,4-tetrahydroisoquinoline: The First Orexin-2 Receptor Selective Nonpeptidic Antagonist". Bioorganic & Medicinal Chemistry Letters 13 (2003) 4497-4499.
Houghton, Alan N. "Mouse monoclonal IgG3 antibody detesting GD3 ganglioside: A phase I trial in patients with malignant melanoma". Proc. Natl. Acad. Sci. USA vol. 62, pp. 1242-1246, Feb. 1985.
Hu, Chang-Deng. "Simultaneous visualization of multipte protein Interactions in living cells using multicolor fluorescence complementation analysis", Nature, May 2003, vol. 21, pp. 539-545.
Huang, Zhenhua, "Anglotensin II Type 1 and Bradykinin B2 Receptors Expressed in Early Stage Epithelial Cells Derived From Human Embryonic Stem Cells", J. Cell, Physiol. 211: 816-825, 2007.
Huttenrauch, Freiderike, G Protein-couple Receptor Kinases Promote Phosphorylation and b-Arreslin-mediated Internalization of CCR5 Homo- and Hetero-oligomers The Journal of Biological Chemistry. vol. 280, No. 45, pp. 37503-37515, Nov. 11, 2005.
Inouye, Satoshi, "The Use of Renilla Luciferase, Oplophonus Luciferase, and Aposequorin as Bioluminescent Receptor Protein in the Presence of Coelanterazine Analogues as Substrate". Biochemical and and Biophysical Research Communications 233, 349-353 (1997).
Ishihara, Katsuhiko, "Moleculer basis of the cell specificity of cytokine action". Biochimica et Biophysica Acta 1592 (2002) 281-296.
Ishii, Yoshiharu, "Effects of the State of the Succinimido-Ring on the Fluorescence and Structrural Properties of Pyrene Maleimide-Labeled aa-Tropomyosin". Biophys. J. e Biophysical Society. vol. 50, Jul. 1986. 75-80.
James, John R. "A rigorous experimental framework for detecting protein oligomerization using bioluminescence resonance energy transfer", Nature. Advance Online Publication. Nov. 5, 2006, pp. 1-6.
Jensen, Anders A. "Probing intermolecular protein-protein interactions in the calcium-sensing receptor homodimer using bioluminescence resonance energy transfer (BRET)", Eur. J. Biochem, 269, 5076-5087 (2002).
Jordan, Bryen A. "G-protein-coupled receptor heterodimerization modulates receptor function". Nature. vol. 399, Jun. 17, 1999. pp. 697-700.
Karniya, Toshio, "Oligomerization of adenosine A2A and dopamine D2 receptors in living cells". Biochemical and Biophysical Research Communications 306 (2003) 544-549.

Kok, Simon W. "Altered setting of the pituitary-thyroid enemble in hypocretin-deficient narcoleptic men", Am J Physiol Encocrinol Metab 288:E892-E899, 2005, First published Dec. 29, 2004.
Kreider, Margaret S, "Immunohistochemical Localization of TRH in Rat CNS: Cimparison With RIA Studies", Peptides, vol. 6, pp. 997-1000, 1985.
Kroeger, Karen M. "G-protein coupled receptor oligomerization in neuroendocrine pathways". Frontiers in Neuroendocrinology 24 (2004) 254-278.
Lu, Xin. "Chamokine (C-C Motif) Ligand 2 Engages CCR2 Stromal Cells of Monocytic Origin to Promote Breast Cancer Metastasis to Lung and Bone". The Journal of Biological Chemistry vol. 284, No. 42, pp. 29087-29096.
Lang, Manja. "Structure-Activity Studies of Orexin A and Orexin B at the Human Orexin 1 and Orexin 2 Receptors Led to Orexin 2 Receptor Selective and Orexin 1 Receptor Preferring Ligands", J. Med. Chem. 2004, 47, 1153-1160.
Langmead, Christopher J. "Characterisation of the binding of [3H]-SB-674042, a novel nonpeptide antegonist, to the human orexin-1 receptor". British Journal of Pharmacology (2004) 141, 340-346.
Lefevre, Charles. "Texas Red-X and Rhodamine Red-X, New Derivatives of Sulforhodamine 101 and Lissamine Rhodamine B with Improved Labeling and Fluorescence Properties", Bioconjugate Chem. 1996, 7, 482-489.
Levi, Jelena. "Bisdeocycoelenterazine Derivatives for Improvements of Bioluminescence Resonance Energy Transfer Assays", J. Am. Chem. Soc. 2007, 129, 11900-11901.
Levoye, Angelique. "The orphan GPR50 receptor specifically inhibits MT1 melatonin receptor function through heterodimerization", The EMBO Journal (2006) 25, 3012-3023.
Levoye, Angelique. "Do orphan G-protein-coupled receptors have ligand-independent functions? New insights from receptor heterodimers". EMBO reports. vol. 7, No. 11, 2006. pp. 1094 -1098.
Loening, Andreas Markus. "Consensus guided mutagenesis of Renilla luciferase yields enhanced stability and ligh output". Protein Engineering, Design & Selection vol. 19, No. 9, pp. 391-400, 2008.
Loening, Andreas Markus, "Red-shifted Renilla reniformis luciferase variants for imaging in living subjects", Nature Methods, Aug. 2007, vol. 4, No. 8. pp. 641-643.
Lorenz, W. Walter. "Isolation and expression of a cDNA encoding Renilla reniformis luciferase", Proc. Natl. Acad. Sci. USA. vol. 88, pp. 4438-4442, May 1991.
Masse, Jacques, "A Prospective Longitudinal Study of Platelet Angiotensin II Receptors for the Prediction of Preeclampsia". PII S00009-9120(98)00021-6.
Matz, Mikhail V. "FLuorescent proteins from nonbioluminescent *Anthozoa* species". Nature Biotechnology, vol. 17, 1999. pp. 969-973.
McAtee, Laura C. "Novel substituted 4-phenyl-[1,3]dioxanes: potent and selctive orexin receptor 2 (OX2R) antagonists", Bioorganic & Medicinal Chemistry Letters 14 (2004) 4225-4229.
Mellado, Mario, "Chemokine receptor homo- or heterodimerization activates distinct signaling pathways". The EMBO Journal vol. 28, No. 10 pp. 2497-2507, 2001.
Marcier, Jean-Francois. "Quantitative Assessment of b1- and b2-Adreneric Receptor Homo- and Heterodimerization by Bioluminescence Resonance Energy Tranfer". The Journal of Biological Chemistry vol. 277, No. 47, Issue of Nov. 22, pp. 44925-44931, 2002.
Milligan, Graeme. "Applications of bioluminescence- and fluorescence resonance energy transfer to drug discovery at G protein-coupled receptors". European Journal of Pharmaceutical Sciences 21 (2004) 397-405.
Milligan, Graeme. "G-protein-coupled receptor heterodimers: Pharmacology, function and relevance to drug discovery", Drug Discovery Today, vol. 11, No. 11-12, Jun. 2006. pp. 541-549.
Milligan, Graeme. "Oligomerisation of G-protein-coupled receptors", Journal of Cell Science, 2001, 114, 1265-1271.
Milligan, Graeme, "G Protein-Coupled Receptor Dimerization: Function and Ligand Pharmacology". Molecular Pharmacology vol. 66, No. 1. pp. 1-7, 2004.

(56) References Cited

OTHER PUBLICATIONS

Milligan, Graeme. "Selectivity in the Oligomerisation of G protein-coupled receptors". Seminars in Cell & Developmental Biology 15 (2004) 263-268.
Milligan, Graeme. "Methods to monitor the quaternary structure of G protein-coupled receptors". FEBS Journal 272 (2005) 2914-2925.
Milligan, Graeme. "Oligomeric structure of the a1b-adranoceptor: Comparisons with rhodopsin", Vision Research 46 (2006) 4434-4441.
Milligan, Graeme. "The specificity and molecular basis of alpha1-adrenoceptor CXCR chemokine receptor dimerization". J Mol Neurosci. 2005; 26(2-3):161-8.
Milligan, Graeme. "The role of GPCR dimerization/oligomerisation in receptor signaling". Ernst Schering Found Symp Proc. 2006;(2):145-61.
Milligan, Graema, "GPCR dimerization", Life Sciences 74 (2003) 181-188.
Murphy, John R. "Genetic construction, expression, and melanoma-selective cytotoxicity of a diphtheria toxin-related a-melanocyte-stimulating hormone fusion protein", Proc. Natl. Acad. Sci. USA vol. 83, pp. 8258-8262, Nov. 1986.
Nagai, Takeharu, "A Variant of Yellow Fluorescent protein with fast and efficient maturation for cell-biological applications". Nature Biotech, vol. 20, Jan. 2002. pp. 87-90.
Nishino, Seiji. "Effects of Thyrotropin-Releasing Hormone and Its Analogs on Daytime Sleapiness and Cataplexy in Canine Narcolepsy". The Journal of Neuroscience, Aug. 15, 1997, 17(16):6401-6408.
Okabe, Masaru. "Green mice' as a source of ubiquitous green cells", FEBS Letters 407 ( 1997) 313-319.
Overton, Mark C. "Use of fluorescence resonance energy transfer to analyze oligomerization of G-protein-coupled receptors expressed in year". Methods 27 (2002) 324-332.
Paulmurugan, R. "Monitoring Protein-Protein InteractionsUsing Split Synthetic Renilla Luciferase Protein-Fragment Assisted Complementation". Anal. Chem. 2003, 75. 1584-1589.
Percherancier, Yann. "Bioluminescence Resonance Energy Transfer Reveals Ligand-induced Conformational Changes in CXCR4 Homo- and Heterodimers", The Journal of Biological Chemistry vol. 280, No. 11, Issue of Mar. 18, pp. 9895-9903, 2005.
Perroy, Julie. "Real-time monitoring of ubiquitination in living cells by BRET", Nature Methods, vol. 1, No. 3, Dec. 2004. pp. 203-208.
Pfleger, Kevin. "New Technologies, Bioluminescence Resonance Energy Transfer (BRET) for the Detection of Real Time Interactions Involving G-Protein Coupled Receptors". Pituitary 6: 141-151, 2003.
Pfleger, Kevin. "Extended bioluminescence resonance energy transfer (eBRET) for monitoring prolonged-protein protein interactions in live cells", Cellular Signalling 18 (2006) 1664-1670.
Pfleger, Kevin, "Illuminating insights into protein-protein interactions using bioluminescence resonance energy transfer (BRET)", Nature Methods, vol. 3, No. 3, Mar. 2006 pp. 165-174.
Pfleger, Kevin. "Bioluminescence resonance energy transfer (BRET) for the real-time detection of protein-protein interactions". Nature Protocols. vol. 1, No. 1, pp. 337-345.
Pflager, Kevin. "Monitoring the formation of dynamic G-protein-coupled receptor-protein complexes living cells", Biochem. J. (2005) 385, 625-637 (Printed in Great Britain).
Pouliot, Lynda, "Platelet Angiotensin II Binding Sites and Early Detection of Preoclampsia". Obstetrics & Gnecolooy, vol. 91, No. 4, Apr. 1998, pp. 591-595.
Prinster, Steven C. "Heterodimerization of G Protein-Coupled Receptors: Specificity and Functional Significance", Pharmacol Rev 57:289-298, 2005.
Quitterer, U. "AT1 receptor heterodimers and angiotensin II responsiveness in preedampsia". Semin Nephrol. Mar. 2004; 24(2):115-9.
Ramsay, Dooglas, "Homo- and hetero-oligomeric interactions between G-protein-coupled receptors in living cells monitored by two variants of bioluminescence resonance energy transfer (BRET) : hetero-oligomers between receptor subtypes form more efficiently than between less closely related sequences", Biochem. J. (2002) 365, 429-440 (Printed in Great Britain).
Renming, Xie. "Antiepileptic effects of CNK-602A, a novel thyrotropin-releasing analog, on absence-like and tonic seizures of spontaneously epileptic rats", European Journal of Pharmacology, 223 (1992) 185-192.
Riehl, Joyce. "Chronic Oral Administratopm of CG-3703, a Thyrotropin Releasing Hormone Analog, Increases Wake and Decreases Cataplexy in Canine Narcolepsy", Neuropsychopharmacology 2000. vol. 23, No. 1. pp. 34-45.
Rios, C. D. "G-protein-coupled receptor dimerization: modulation of receptor function", Pharmacology & Therapeutics 92 (2001) 71-87.
Rios, Cari. "Interactions Between Delta Opioid Receptor and Alpha 2A Adrenoceptors", Clinical and Experimental Pharmacology and Physiology (2004) 31, 833-836.
Rios, Carl. "delta opioid and CB1 cannabinoid receptor interactions: reciprocal inhibition of receptor signaling and neuritogenesis". British Journal of Pharmacology (2006) 148, 387-395.
Robert, Jessica. "Mechanisms of Cell-surface Rerouting of an Endoplasmic Reticulum-retained Mutant of the Vasopressin V1b/V3 Receptor by a Pharmacological Chaperone", The Journal of Biological Chemistry vol. 280, No. 51, pp. 42198-42206, Dec. 23, 2006.
Rocheville, Magalle. "Receptors for Dopamine and Somatostatin: Formation of Hetero-Oligomers with Enhanced Functional Activity". Science 288, 154-157 (2000).
Rode, Aldo. "Bioluminescence and chemiluminescence in drug screening", Anal Bioanal Chem (2003) 377 : 826-833.
Rodgers, R. J. "SB-334887, a selective orexin-1 receptor antagonist, enhances behavioural satiety and blocks the hyperphagic effect of orexin-A in rats". European Journal of Neuroscience, vol. 13, pp. 1444-1452, 2001.
Rodriguez-Frade, Jose Miguel. "Blocking HIV-1 infection via CCR5 and CXCR4 receptor by acting in trans on the CCR2 chemokine repeptor", The EMBO Journal (2004) 23, 66-76.
Sakurai, Takeshi. "Orexins and Orexin Receptors: A Family of Hypothalamic Neuropeptide G and Protein-Coupled Receptors that Regulate Feeding Behavior", Cell, vol. 92, 573-585, Feb. 20, 1998.
Sakurai, Takeshi, "Roles of orexin/hypocretin in regulation of sleep/wakefulness and energy homeostasis", Sleep Medicine Reviews (2005) 9, 231-241.
Salahpour, Ali. "Homodimerization of the b2-Adrenergic Receptor as a Prerequisite for Cell Surface Targeting", The Journal of Biological Chemistry vol. 279, No. 32, Issue of Aug. 6, pp. 33390-33397, 2004.
Shah, Dinesh M. "Role of the renin-angiotensin system in the pathogenesis of preeclampsia". Am J Physiol Renal Physiol 288: F614-F625, 2005.
Shaner, Nathan C. "A guide to choosing fluorescent proteins". Nature Methods. vol. 2, No. 12, Dec. 2005, pp. 905-909.
Shimomura, Osamu. "Membrane permeability of coelenferazine analogues measured with fish eggs". Biochem. J. (1997) 326, 297-298 (Printed in Great Britain).
Small, Kersten M. "(a2A- and a2C-AdrenergicReceptors Form Homo- and Heterodimers: The Heterodimeric State Impairs Agonist-Promoted GRK Phosphorylation and b-Arrestin Recruitment". Biochemistry 2006, 45, 4760-4767.
Song, Gyun Jee. "Regulated Dimerization of the Thyrotropin-Releasing Hormone Receptor Affects Receptor Trafficking But Not Signaling". Mol. Endocrinol. 2005 19:2859-2870.
Springael, Jean-Yves. "Dmerization of chemokine receptors and its functional consequences", Cytokine & Growth Factor Reviews 16 (2005) 611-623.
Springael, Jean-Yves. "Allosteric Modulation of Binding Properties between Units of Chemokine Receptors Homo- and Hetero-Oligomers". Molecular Pharmacology vol. 69, No. 5, pp. 1652-1661.
Starr-Spires, Linda D. "HIV-1 entry and entry inhibitors as therapeutic agents". Clin Lab Med 22 (2002) 681-701.
Storez, Helene, "Homo- and Hetero-oligomerization of b-Arrestings in Living Cells", The Journal of biological Chemistry vol. 280, No. 48, pp. 40210-40215, Dec. 2, 2005.

(56) References Cited

OTHER PUBLICATIONS

Stranick, Kimberly S. "Identification of Transcription Factor Binding Sites Important in the Regulation of the Human Interleukin-5 Gene". The Journal of Biological Chemistry vol. 272, No. 26, Issue of Jun. 27, pp. 16453-16465, 1997.

Tateyama, Michihiro, "Ligand-induced rearrangement of the dimeric metabotropic glutamate receptor 1α". Nature Structural & Molecular Biology. vol. 11, No. 7, Jul. 2004, pp. 637-642.

Terrillon, Sonia. "Oxytocin and Vasopressin V1a and V2 Receptors Form Constitutive Homo- and Heterodimers during Biosynthesis". Mol. Endocrinol. 2003 17:677-691 originally published online Dec. 23, 2002.

Terrillon, Sonia, "Heterodimerization of V1a and V2 vasopressin receptors datermines the interaction with b-arrestin and their trafficking patterns". PNAS, vol. 101, No. 6, Feb. 2004, pp. 1548-1553.

Terrillon, Sonia. "Receptor activity-independent recruitment of barrestin2 reveals specific signaling modes". The EMBO Journal (2004) 23, 3950-3961.

Terrillon, Sonia, "Roles of G-protein-coupled receptor dimerization". EMBO reports. vol. 5, No. 1, 2004. pp. 30-34.

Thevenin, Demien. "Oligomerization of the fifth tramsmembrane domain from the adenosine A2A receptor". Protein Science (2005), 14:2177-2186.

Torvinen, Maria. "Adenosine A2A Receptor and Dopamine D3 Receptor Interactions: Evidence of Functional A2A/D3 Heteromeric Complexes". Mol Pharmacol 67:400-407, 2005.

Toth, Peter T. "Regulation CXCR4 Receptor Dimerization by the Chemokine SDF-1a and HIV-1 Coat Protein gp120: A Fluorescence Resonance Energy Transfer (FRET) Study", JPET 310:8-17, 2004.

Tsien, Roger Y. "The Green Fluorescent Protein". Annu. Rev, Biochem. 1998. 67:509-44.

Verhaegen, Monique. "Recombinant Gaussia Luciferase. Overexpression, Purification, and Analytical Application of a Bioluminescent Reporter for DNA Hybridization", Anal. Chem. 2002, 74, 4378-4385.

Waldhoer, Maria. "A heterodimer-selective agonist shows in vivo relevance of G protein-coupled receptor dimers". PNAS. vol. 102, No. 25. Jun. 2005. pp. 9050-9055.

Wang, Chung-Yin, "Activation of the Granulocyte-Macrophage Colony-Stimulating Factor Promoter in T Cells Requires Cooperative Binding of Elf-1 and AP-1 Transcription Factors", Molecular and Cellular Biology, Feb. 1994, p. 1153-1159. vol. 14, No. 2

Wang, Qing-Ping. "The orexinergic synaptic Innervation of serotonin- end orexin 1-receptor-containing neurons in the dorsal raphe nucleus". Regulatory Peptides 126 (2005) 35-42.

Wang, Jinhai. "Constitutive Association of Cell Surface CCR5 and CXCR4 in the Presence of CD4". Journal of Cellular Biochemistry 93:753-760 (2004).

Wang, Danxin. "Opioid Receptor Homo- and Heterodimerization in Living Cells by Quantitative Bioluminescence Resonance Energy Transfer". Mol Pharmacol 67:2173-2184, 2005.

Wang, Jinhai, "Dimerization of CXCR4 in living malignant cells: control of cell migration by a synthetic peptide that reduces homologous CXCR4 interactions". Mol Cancer Ther 2006:5:2474-2483. Published online Oct. 13, 2008.

Wilson, Shirley. "The CXCR1 and CXCR2 Receptors Form Contitutive Homo- and Heterodimers Selectively and with Equal Apparent Affinities". The Journal of Biological Chemistry vol. 280, No. 31, Issue of Aug. 5, pp. 28663-28674, 2005.

Wolberger, Cynthis. "Multiprotein-DNA Complexes in Transcriptional Regulation". Annu. Rev. Biophys. Biomol. Struct. 1999. 28:29-56.

Wu, P. "Resonance energy transfer: methods and applications". Anal Biochem. Apr. 1994; 218(1):1-13.

Xu, Yao. "A bioluminescence resonance energy transfer (BRET) system: Application to interacting circadian clock proteins". Proc. Natl. Acad. Sci. USA vol. 96, pp. 151-156, Jan. 1999.

Yayama, Katsutoshi. "Angiotensin-Converting Enzyme Inhibitor Enhances Liver Regeneration Following Partial Hepatectomy: Involvement of Bradykinin B2 and Angiotensin AT1 Receptors", Biol. Pharm. Bull. 30(3) 591-594 (2007).

Zacharlas, David A. "Partitioning of Lipid-Modified Monomeric GFPs into Membrane Microdomains of Live Cells", Science 296, 913 (2002).

Zemicka-Goetz, M. "Following cell fate in the living mouse embryo". Development 124, 1133-1137 (1997) Printed in Great Britain.

Zhang, Jin. "Creating New Fluorescent Probes for Cell Biology". Nature. vol. 3, Dec. 2002. pp. 906-918.

International Preliminary Report on Patentability for Corresponding International Application No. PCT/AU2007/001722 dated May 12, 2009, pp. 1-7.

International Search Report and Written Opinion for Corresponding International Application No. PCT/AU2007/01722 dated Jan. 15, 2008, pp. 1-6.

Merrifield, R.B. Solid Phase Synthesis. I. The Syntehsis of a Tetrapeptide. J. Am Chem. Soc. Jan. 31, 1963. vol. 85, pp. 2149-2154.

Kroeger, Karen M. et al. Constitutive and Agonist-dependent Homo-oligomerization of the Thyrotropin-releasing Hormone Receptor. The Journal of Biological Chemistry. Apr. 20, 2001, vol. 276, No. 16, pp. 12738-12743.

Milligan, G. et al. G Protein-Coupled Receptor Fusion Proteins in Drug Discovery. Current Pharmaceutical Design, 2004, 10, pp. 1989-2001.

Nabah, Yafa Naim Abu et al. CXCR2 Blockade Impairs Angiotensin II-Induced CC Chemokine Synthesis and Mononuclear Leukocyte Infiltration. Arterioscier Thrombosis and Vascular Biology (2007) 27, pp. 2370-2376.

Tsukuda, Kana et al. Irbesartan attenuates ischemic brain damage by inhibition of MCP-1/CCR2 signaling pathway beyond AT1 receptor blockade. Biochemical and Biophysical Research Communication, (2011) 409, pp. 275-279.

Urushihara, Maki et al. Addition of Angiotensin II Type 1 Receptor Blocker to CCR2 Antagonist Markedly Attenuates Crescentic Glomerulonephritis. Hypertension, Mar. 2011, 57 (3), pp. 586-593.

Huijun et al., "Clinical Effect Observation of Irbesartan in Treating Type 2 Diabetic Nephropathy", Cilinical Medical Engineering; 2010, vol. 17, Issue 6, pp. 28-29.

Xiu-Juan et al., "Cysteine-cysteine chemokine and diabetic nephropathy", 2009, International Journal of Internal Medicine, vol. 36, Issue 4, pp. 192-195.

Dol et al., "Angiotensin AT1 Receptor Irbedartan Decreases Lesion Size, Chemokine Expression, and Macrophage Accumulation in Apolipoprotein E-Deficient Mice", Journal of Cardiovascular Pharmacology, May 2, 2001, vol. 38, pp. 395-405.

Yamashita et al., "Propagermanium Reduces Atherosclerosis in Apolipoprotein E Knockout Mice via Inhibition of Macrophage Infiltration", Arterioscler Thromb. Vasc. Bio., Apr. 1, 2002, vol. 22, pp. 969-974.

Urushihara et al., "Addition of Angiotensin II Type 1 Receptor Blocker to CCR2 Antagonist Markedly Attenuates Crescentic Glomerulonephritis", Hypertension, vol. 56, No. 5, Abstract from the American Journal of Nephrology Renal Week Conference held on Oct. 13-16, 2010 in Washington D.C., p. e161, No. P510.

Chen et al., "Angiotensin II Induces Monocyte Chemoattractant Protein-1 Gene Expression in Rat Vascular Smooth Muscle Cells," Circulation Research, 1998, 83, 952-959.

Yamashita et al., "Propagermanium Reduces Atherosclerosis in Apolipoprotein E Knockout Mice via Inhibition of Macrophage Infiltration," Arteriosclerosis, Thrombosis, and Vascular Biology, 2002, 22, 969-974.

Dol et al., Angiotensin AT1 Receptor Antagonist Irbesartan Decreases Lesion Size, Chemokine Expression, and Macrophage Accumulation in Apolipoprotein E-Deficient Mice, Journal of Cardiovascular Pharmacology, 2001, 38(3), 395-405.

Atkins et al., "Proteinuria Reduction and Progression to Renal Failure in Patients With Type 2 Diabetes Mellitus and Overt Nephropathy", American Journal of Kidney Diseases, Feb. 2005, vol. 45, No. 2, pp. 281-287.

Third Party Observation filed in European Application No. EP 12 734 251.7 dated Mar. 28, 2017, 18 Pages.

(56) References Cited

OTHER PUBLICATIONS

Urushihara et al., "Combination Therapy with CCR2 Antagonist and Angiotensin II Type 1 Receptor Blocker Markedly Ameliorates Crescentic Glomerulonephritis", J Am Soc Nephrp, 2010, vol. 21, Abstract from the High Blood Pressure Research Conference held on Nov. 18, 2010, p. 272A, entry TH-P0703, with unconfirmed online publication date of Oct. 20, 2010.

Urushihara et al., "Addition of Angiotensin II Type 1 Receptor Blocker to CCR2 Antagonist Markedly Attenuates Crescentic Glomerulonephritis", Hypertension, vol. 56, No. 5, Abstract from the American Journal of Nephrology Renal Neek Conference held on Oct. 13-16, 2010 in Washington D.C., p. e161, entry P510, published Oct. 20, 2010.

Office Action dated Jun. 18, 2019 for Japanese Application No. 2018-101282, 8 pages, including English translation.

Gandhi et al., "Effects of Eprosartan on Glomerular Injury in Rats with Reduced Renal Mass", Pharmacology, 1999, vol. 59, No. 2, pp. 89-94.

Yakkyoku, "ARB", Medical Online, 2010, vol. 61, No. 12, pp. 28-33. (See page 1 (last paragraph) of the translation of Japanese Office Action dated Jun. 18, 2019 for a concise explanation of the relevance of this document, which is referred to as Reference 2 in the Office Action).

Masuda et al., "Effects of angiotensin II type 1 receptor blacker on ambulatory blood pressure variability in hypertensive patients with overt diabetic nephropathy", Hypertension Research, 2009, vol. 32, No. 11, pp. 950-955.

Burnshishinketsukanbyou, "Smart", Evidence Based Medicine, 2008, vol. 9, No. 2, pp. 62 to 66. (See p. 2 (paragraph 2) of the translation of Japanese Office Action dated Jun. 18, 2019 for a concise explanation of the relevance of this document, which is referred to as Reference 4 in the Office Action).

Hirobumi Tokuyama, "Dose Dependent Effect of ARB on Renoprotection in Chronic Glomerulonephritis", J. New. Rem. & Clin., 2003, vol. 52, No. 10, pp. 53-57 with English abstract.

Ketsuatsu, Medical Online, 2010, vol. 17, No. 8, pp. 44 to 49. (See p. 2 (paragraph 4) of the translation of Japanese Office Action dated Jun. 18, 2019 for a concise explanation of the relevance of this document, which is referred to as Reference 6 in the Office Action).

\* cited by examiner

*P <0.05 Vs sham
P <0.05 Vs un-treated STNx
ƒP <0.05 Vs STNx+Irb

*p<0.05 vs sham p<0.05 vs STNx+Irb

COMBINATION THERAPY

CROSS-REFERENCE TO RELATED APPLICATIONS

This application is a Continuation of U.S. application Ser. No. 15/086,823 filed 31 Mar. 2016 (pending), which is a Divisional of U.S. application Ser. No. 13/979,127 filed 10 Jul. 2013, now U.S. Pat. No. 9,314,450 issued 19 Apr. 2016, which is a U.S. National Stage application of PCT/AU2012/000014 filed 11 Jan. 2012, which claims priority to Australian patent application 2011900060 filed 11 Jan. 2011, U.S. provisional application 61/432,896 filed 14 Jan. 2011, Australian patent application 2011904279 filed 17 Oct. 2011, and U.S. provisional application 61/547,951 filed 17 Oct. 2011, the entire disclosures of which are hereby incorporated by reference in their entireties.

FIELD OF THE INVENTION

The present invention relates to a combination therapy, comprising at least one chemokine receptor pathway inhibitor and at least one angiotensin receptor blocker.

BACKGROUND ART

Proteins do not act in isolation in a cell, but in stable or transitory complexes, with protein-protein interactions being key determinants of protein function (Auerbach et al., (2002), *Proteomics* 2:611-623). Furthermore, proteins and protein complexes interact with other cellular components like DNA, RNA and small molecules. Understanding both the individual proteins involved in these interactions and their interactions are important for a better understanding of biological processes.

The primary physiological function of chemokines reported by Allen (Allen, S. et al. (2007) *Annual Review Immunology* 25:787-820) is the regulation of "cell migration during routine immune surveillance, inflammation and development". Chemokines are released in response to proinflammatory cytokines and selectively bind to a large family of G protein-coupled receptors, which mediate the physiological responses to chemokines. Chemokines were originally referred to as chemotactic cytokines.

Since discovering that the chemokine system plays an integral role in human immunodeficiency virus (HIV) infection and the pathogenesis of acquired immune deficiency syndrome (AIDS), considerable efforts have been made to understand the underlying mechanism(s) involved in order to develop potential intervention strategies (Lusso, P. (2006) *EMBO Journal* 25:447-456). Furthermore, any deleterious immune response associated with a particular condition, including asthma, almost invariably result from a dysfunctional chemokine system. The pathogenesis of atherosclerosis has also been shown to involve chemokine signaling pathways, with the infiltration of macrophages into arterial lesions directly contributing to this aberrant inflammatory disorder (Boisvert, W. (2004) *Trends in Cardiovascular Medicine* 14:161-165).

Animal model studies of chronic inflammatory diseases have demonstrated that inhibition of binding between MCP-1 (monocyte chemotactic protein-1, also known as monocyte chemoattractant protein-1, monocyte chemotactic and activating factor (MCAF) and chemokine (C-C motif) ligand 2 (CCL2)) and CCR2 (chemokine (C-C motif) receptor 2) by an antagonist suppresses the inflammatory response. The interaction between MCP-1 and CCR2 has been implicated (see Rollins B J (1996) *Mol. Med. Today*, 2:198; and Dawson J, et al., (2003) *Expert Opin. Ther. Targets*, 7(1):35-48) in inflammatory disease pathologies such as uveitis, atherosclerosis, rheumatoid arthritis, multiple sclerosis, Crohn's Disease, nephritis, organ allograft rejection, fibroid lung, renal insufficiency, diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, allergic asthma, periodontal diseases, periodontitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

Monocyte migration is inhibited by MCP-1 antagonists (either antibodies or soluble, inactive fragments of MCP-1), which have been shown to inhibit the development of arthritis, asthma, and uveitis. Propagermanium (3-oxygermylpropionic acid polymer), a molecule that has been used as a therapeutic agent against chronic hepatitis, also has been shown to specifically inhibit in vitro chemotactic migration of monocytes by MCP-1 through a mechanism that seems to require glycosylphosphatidylinositol (GPI)-anchored proteins such as CD55, CD59 and CD16 (Yokochi, S. (2001) Journal of Interferon and Cytokine Research 21:389-398).

Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to upregulate) the expression of MCP-1 and other chemokines in the nasal mucosa of people with allergic rhinitis, suggesting the presence of a positive feedback loop in such patients.

Kidney disease is associated with chronic inflammation characterised by the accumulation of kidney macrophages. The production of monocyte chemoattractant protein-1 (MCP-1/CCL2) by diabetic kidneys has been identified as a major factor influencing macrophage accumulation in the kidney disease arising from diabetic nephropathy (see Tesch G H (2008) MCP-1/CCL2: a new diagnostic marker and therapeutic target for progressive renal injury in diabetic nephropathy Am J Physiol Renal Physiol 294:697-701). In various animal models inhibition of CCR2 and/or inhibition of specific CCR2 pathways and/or inhibition of the CCR2 ligand MCP-1 has been shown to reduce kidney damage (see Tesch (2008) above; Rao V et al (2006) Role for Macrophage Metalloelastase in Glomerular Basement Membrane Damage Associated with Alport Syndrome, American Journal of Pathology, Vol. 169(1) 32-46; Kang Y S (2010) CCR2 antagonism improves insulin resistance, lipid metabolism, and diabetic nephropathy in type 2 diabetic mice Kidney International 78, 883-894; Kitagawa K (2004) Blockade of CCR2 Ameliorates Progressive Fibrosis in Kidney, American Journal of Pathology, Vol. 165(1) 237-246; Park J (2008) MCP-1/CCR2 system is involved in high glucose-induced fibronectin and type IV collagen expression in cultured mesangial cells, Am J Physiol Renal Physiol 295: F749-F757).

Tesch (2008) notes that selective targeting of MCP-1 has been proven to be an effective treatment in suppressing animal models of kidney disease that include diabetic nephropathy; however, such therapies have not yet been validated in human diabetic nephropathy. Treatments including small molecular antagonists of CCR2 (INCB3344, propagermanium, RS-504393) have been shown to suppress inflammation in mouse models of multiple sclerosis, renal ischemia-reperfusion injury, ureter obstruction, and diabetic nephropathy and in a rat model of arthritis; Engineered biological antagonists of CCR2 have also proven effective; Subcutaneous infusion of cells transfected with a vector expressing a truncated inactive form of MCP-1 has been found to suppress the development of renal inflammation in a mouse model of lupus nephritis. Similarly, muscle transfection with 7ND (a mutant of MCP-1) reduces renal inflammation in mouse models of renal ischemia-reperfusion injury, lupus nephritis, and diabetic nephropathy. Human trials of chemokine monotherapies for inflammatory diseases, to date, have not lead to drug approvals. Anders A-J et al considers reasons why single chemokine antagonist treatments have not been effective in disease treatments and discuss possible explanations including redundancy of single chemokine mediators and variable expression patterns of chemokine receptors. (see Anders A-J et al (2009) Questions about Chemokine and Chemokine Receptor Antagonism in Renal Inflammation, Nephron Exp Nephrol 2010; 114:e33-e38). Therefore, there exists a need in the art for an effective treatment of diseases that are caused through the CCR2 pathways.

The renin-angiotensin system (RAS) plays an important role in the sympathetic nervous system and fluid homeostasis. Renin is a proteolytic enzyme secreted by the kidneys that mediates the formation of angiotensin I (AngI) from a globulin precursor, angiotensinogen (Rang, H. P., et al., Pharmacology: $3^{rd}$ Edition, 1995, Published by Churchill Livingstone, Edinburgh, UK.). AngI itself appears to have little physiological importance other than providing a substrate for a second enzyme, angiotensin-converting enzyme (ACE), which converts AngI to the highly active angiotensin II (AngII). However, it should be noted that AngII can be generated by alternative, ACE-independent mechanisms. AngII can in turn be metabolised to AngIII by aminopeptidases.

AngII is an extremely potent vasoconstrictor and as a consequence it has been extensively studied in the context of heart disease and hypertension pathogenesis (Ramasubbu, K. (2007) *Cardiology Clinics* 25:573-580).

Chronic renal disease is a major cause of mortality and morbidity, however the basic cellular events that promote its progression remain elusive and it is likely that proinflammatory mediators, leading to inflammation, hypoxia and increased extracellular matrix (ECM) deposition are a major cause of renal failure (Gilbert (1999) *Kidney Int* 56:1627-1637, 1999). These pathological events are accompanied by proteinuria and a decline in glomerular filtration rate (GFR), ultimately leading to end-staged renal failure. Although angiotensin-converting enzyme inhibitors (ACEi) and angiotensin receptor blockers are now viewed as first line treatment for chronic renal disease and have clearly been shown to confer renoprotection, chronic renal disease remains a progressive disorder, which ultimately leads to renal failure. In the collaborative study group trial (Lewis (1993). The effect of angiotensin converting enzyme inhibition on diabetic nephropathy. New England Journal of Medicine 329:1456-1462), captopril therapy, although retarding the decline in renal failure, did not halt the progression of diabetic nephropathy in the vast majority of patients. In contrast to the clinical setting, experimental studies of renoprotective agents have mostly shown complete amelioration of renal structural and functional abnormalities in commonly used models of diabetic nephropathy. A major advantage of the diabetic Ren-2 rat and the Sub Total nephrectomy (STNx) model is that as is observed in man, ACEi or angiotensin receptor blockers attenuate but do not prevent the development of renal failure (Kelly (1998) *Kidney Int* 54:343-352, and Kelly (2000) *Kidney Int* 57:1882-1894). Furthermore, the diabetic Ren-2 rat and STNx models can be used to study additional therapies which have the potential to further improve the outlook in renal disease progression in the context of concomitant ACEi or angiotensin receptor blockade.

The renin-angiotensin system (RAS), a hormonal cascade involved in blood pressure control, electrolyte homeostasis and cell growth and death, exists in the kidney at two major sites: the glomerulus and proximal tubules. The RAS has been implicated in the progression of kidney disease as blockade of this system attenuates proteinuria and glomerular and tubulointerstitial disease in both human and experimental diabetes Lewis (1993). The renoprotective effect of RAS blockers have been attributed to their ability to reduce glomerular pressure (Zatz (1985) Predominance of hemodynamic rather than metabolic factors in the pathogenesis of diabetic nephropathy. PNAS 82:5963-5967). However it has been recognized that local increases in angiotensin II can induce sclerosis and inflammation through its cell growth promoting properties (Wolf (1993) Angiotensin II as a renal growth factor. J Am Soc Nephrol 3:1531-1540). There is ample evidence from studies of various glomerular diseases that Ang II exerts cell injury by the up-regulation of other growth factors (Ruiz Ortega (1994) Involvement of angiotensin II and endothelin in matrix protein production and renal sclerosis. J Hypertens Suppl. 12:S51-S58) such as transforming growth factor-β (TGF-β). Indeed, these growth factors are produced by the kidney and are increased by Ang II, inducing cell proliferation, cell cycle arrest, and death, alterations in cell phenotype and ECM accumulation (Kelly (1998), Kelly (2000) and Kelly (2002)). Although evidence suggests that Ang II induces a variety of responses by the upregulation of growth factors, very few studies have described how Ang II promotes activation of the growth factors in the diabetic setting (Naito (2004) *Am J Physiol Renal Physiol* 286:F278-F287).

The efficacy of the angiotensin receptor blocker irbesartan ($AT_1R$, market name Avapro®, SanofiAventis) in the management of diabetic nephropathy in patients with hypertension has been evaluated in two large (n>500), randomized, double-blind, placebo-controlled, multinational trials, IRMA 2 (Irbesartan Microalbuminuria Type 2 Diabetes in Hypertensive Patients) (Parving (2001) *N Engl J Med* 345 (12): 870-8 and IDNT (Irbesartan Diabetic Nephropathy Trial) Lewis (2001) *N Engl J Med* 345 (12): 851-60).

In order to counter the deleterious vasoconstrictor effects of AngII in patients with hypertension [onset of end stage renal disease], therapeutic strategies have been developed that intervene at the level of AngII signalling. In particular, compounds that inhibit the activity of ACE, preventing the conversion of AngI to AngII, and those that specifically block the activation of angiotensin receptors (ATRs), have been employed in the treatment of such conditions (Matchar, D. B. (2008) *Annals of Internal Medicine* 148:16-29).

The inventors have shown the heteromerisation of the angiotensin receptor with members of the chemokine receptor family (WO2010/108232). The inventors have shown that the chemokine receptor associates with the angiotensin receptor as a chemokine receptor/angiotensin receptor hetero-dimer/-oligomer. The inventors have shown that the CCR2 associates with the AT1R as a CCR2/AT1R heterodimer/-oligomer.

Angiotensin and CCR2 signalling pathways have previously been shown to interact. For example: angiotensin II effects on vascular pathologies are attenuated by deficiency of the CCR2 receptor (Daugherty A (2010) *Clin Sci* (Lond). 118(11):681-9; Ishibachi M (2004) *Arteriosclerosis, Thrombosis, and Vascular Biology* 24; Tieu (2011) Aortic Adventitial Fibroblasts Participate in Angiotensin-Induced Vascular Wall Inflammation and Remodelling J Vasc Res 48(3) 261-272).

Furthermore, angiotensin II, which induces MCP-1 expression, increase with age resulting in upregulation of MCP-1 and its receptor CCR2. This upregulation can also occur in various diseases. (Spinetti G (2004) *Arterioscler Thromb Vasc Biol* 24(8): 1397-402).

Angiotensin receptor blockers have been shown to inhibit the expression of MCP-1 and CCR2 (Dai (2007) *British Journal of Pharmacology* 152, 1042-1048).

The inventors have surprisingly found that the administration of an angiotensin receptor blocker together with a chemokine receptor pathway inhibitor overcomes some or all of the shortcomings of the prior art.

The preceding discussion is intended only to facilitate an understanding of the invention. It should not be construed as in any way limiting the scope or application of the following description of the invention, nor should it be construed as an admission that any of the information discussed was within the common general knowledge of the person skilled in the appropriate art at the priority date.

SUMMARY OF THE INVENTION

The present invention provides a pharmaceutical composition comprising:
a) at least one angiotensin receptor blocker or a pharmaceutically acceptable salt thereof, and
b) at least one chemokine receptor pathway inhibitor or a pharmaceutically acceptable salt thereof.

The pharmaceutical composition may optionally further comprise a pharmaceutically acceptable carrier.

In one aspect, the pharmaceutical composition inhibits or partially inhibits arrestin recruitment.

In another aspect, the pharmaceutical composition inhibits or partially inhibits inositol phosphate production.

The invention further provides a method for the treatment, amelioration or prevention of a condition or disease comprising administering to a subject a therapeutically effective amount of a combination of (i) an angiotensin receptor blocker and (ii) a chemokine receptor pathway inhibitor.

In one aspect, the chemokine receptor pathway inhibitor inhibits or partially inhibits a protein other than the chemokine receptor, more preferably, the inhibitor is an agent which blocks MCP-1 induced migration and activation of monocytes and chemotactic migration through the targeting of glycosylphosphatidylinositol (GPI)-anchored proteins such as CD55, CD59 and CD16. Preferably, the chemokine receptor pathway inhibitor is propagermanium. Alternatively, the chemokine receptor pathway inhibitor is RS504393.

Preferably, the angiotensin receptor blocker is irbesartan.

The invention also contemplates the use of a pharmaceutical composition comprising at least one angiotensin receptor blocker or a pharmaceutically acceptable salt thereof, and at least one chemokine receptor pathway inhibitor or a pharmaceutically acceptable salt thereof; for the manufacture of a dosage form for the treatment of a disease.

The pharmaceutical composition may optionally further comprise a pharmaceutically acceptable carrier.

ABBREVIATIONS

Figure 1:
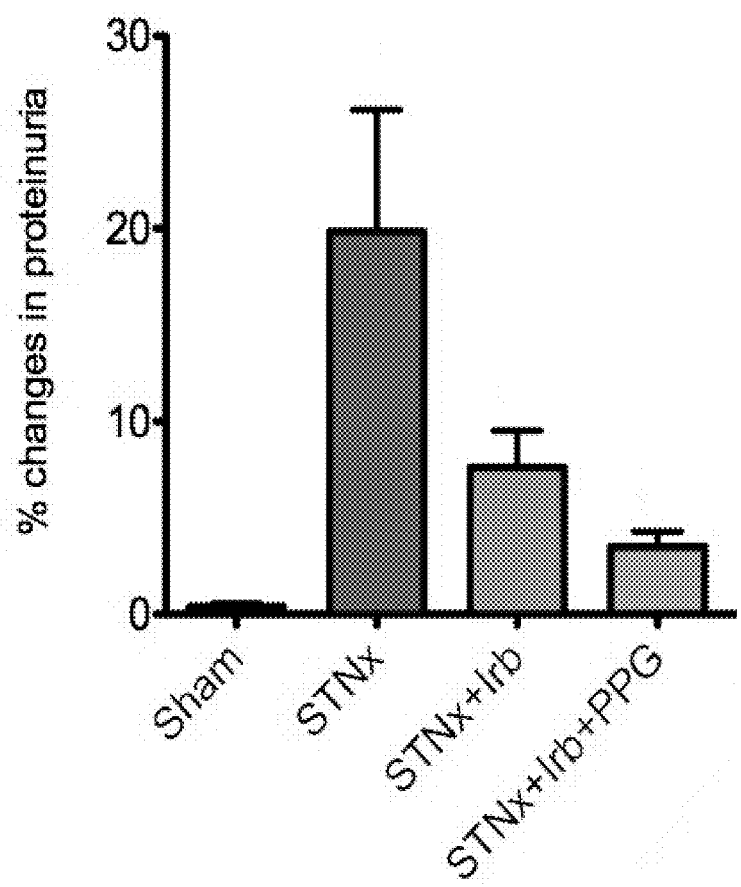
FIG. 1: shows a bar graph of the improvement in levels of proteinurea achieved in the sub-total nephrectomy (STNx) model of end organ renal disease when treated with a combination of Irbesartan (Irb), an angiotensin receptor blocker, and propagermanium (PPG) (a chemokine receptor pathway inhibitor) (low dose) as compared to untreated animals and animals treated with the angiotensin receptor blocker alone as described in Example 1.

ACE Angiotensin-converting enzyme
ACEi Angiotensin-converting enzyme inhibitor
AIDS Acquired immune deficiency syndrome
AngI Angiotensin I peptide
AngII Angiotensin II peptide
AngIII Angiotensin III peptide
$AT_1R$ Angiotensin receptor type 1
$AT_2R$ Angiotensin receptor type 2
barr beta-arrestin.
BP Blood pressure
CCL2 Chemokine (C-C motif) ligand 2
CCRs CC Chemokine receptors
DOP Delta opioid
GFR Glomerular filtration rate
GPCRs G protein-coupled receptors.
HIV Human immunodeficiency virus
KOP Kappa opioid
LPO Lateral preoptic area
MCP-1 Monocyte chemotactic protein-1, also known as monocyte chemoattractant protein-1
NPY Neuropeptide Y.
STNx Sub-total nephrectomy

DESCRIPTION OF THE INVENTION

General

All publications, including patents and patent applications, cited herein, whether supra or infra, are hereby incorporated by reference in their entirety. However, publications mentioned herein are cited for the purpose of describing and disclosing the protocols, reagents and vectors that are reported in the publications and which may be used in connection with the invention. Nothing herein is to be construed as an admission that the invention is not entitled to antedate such disclosure by virtue of prior invention.

As used herein and in the appended claims, the singular forms "a," "an," and "the" include the plural unless the context clearly dictates otherwise. Thus, for example, a reference to "a protein" includes a plurality of such proteins, and a reference to "an analyte" is a reference to one or more analytes, and so forth.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The invention described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

Throughout this specification, unless the context requires otherwise, the word "comprise" or variations, such as "comprises" or "comprising" will be understood to imply the inclusion of a stated integer, or group of integers, but not the exclusion of any other integers or group of integers.

DETAILED DESCRIPTION OF THE INVENTION

Recent studies have shown that G protein-coupled receptors (GPCRs) may not only act as monomers but also as homo- and hetero-dimers and/or homo- and hetero-oligomers (also known as homomers and heteromers), which causes altered ligand binding, signalling and endocytosis (Rios et al. (2000) *Pharmacol. Ther.* 92:71-87). The effect of drugs acting as agonists or antagonists of a specific receptor may therefore depend on the binding partners of this receptor. It may be desirable to limit the effect of a drug to a cellular response mediated by a specific receptor dimer or oligomer.

Instances of different tissues having different repertoires of hetero-dimers have been reported. For example, 6'guanidinoaltrindole, an analogue of a well-known kappa opioid (KOP) receptor ligand, has been identified as a delta opioid-kappa opioid (DOP-KOP) hetero-dimer selective agonist, with efficacy as a spinally selective analgesic, leading to the conclusion that DOP-KOP heterodimers are expressed in the spinal cord, but not in the brain (Waldhoer, M. et al. (2005) *Proc. Natl. Acad. Sci.* USA 102.9050-9055). Accordingly, the hetero-dimeric or hetero-oligomeric receptor, comprising at least one chemokine receptor subunit associated with at least one angiotensin receptor subunit represents a novel drug target.

As is the case with 6'guanidinoaltrindole, known ligands may exhibit differing abilities to trigger a hetero-dimeric receptor, which may uncover new applications for pre-existing molecules:

Hilairet S. et al. 2003 (*J. Biol. Chem.* 27823731-23737) have recently shown that CB1 antagonists suppress appetite by acting through a CB1/OxR1 heteromer pair.

It has been shown that somatostatin SSTR5 receptor will heteromerise with a dopamine D2 receptor (Rocheville M. et al. (2000) *Science* 288:154-157).

Angiotensin and CCR2 signalling pathways have previously been shown to interact. For example, angiotensin II effects on vascular pathologies are attenuated by deficiency of the CCR2 receptor (Daugherty A (2010) *Clin Sci* (Lond). 118(11):681-9; Ishibachi M (2004) *Arteriosclerosis, Thrombosis, and Vascular Biology* 24).

The inventors have shown the heteromerisation of the angiotensin receptor with members of the chemokine receptor family (WO02010/108232).

Whilst these examples show the functional interaction of receptors, they do not identify the specific formulations of combined therapies that may provide improved therapeutic outcomes.

Pharmaceutical Compositions

Preferably, the combination therapy will act through the chemokine receptor pathway and the angiotensin receptor. The present invention therefore provides a pharmaceutical composition comprising:
 a) at least one angiotensin receptor blocker or a pharmaceutically acceptable salt thereof; and
 b) at least one chemokine receptor pathway inhibitor or a pharmaceutically acceptable salt thereof.

The pharmaceutical composition may optionally further comprise a pharmaceutically acceptable carrier.

The phrase "chemokine receptor" is to be understood to at least include the G protein-coupled CC chemokine receptors (CCRs), including: CC chemokine receptor 1 (CCR1), CC chemokine receptor 2 (CCR2), CC chemokine receptor 3 (CCR3), CC chemokine receptor 4 (CCR4), CC chemokine receptor 5 (CCR5), CC chemokine receptor 6 (CCR6), CC chemokine receptor 7 (CCR7), CC chemokine receptor 8 (CCR8), CC chemokine receptor 9 (CCR9), CC chemokine receptor 10 (CCR10). The phrase "chemokine receptor" is also to be understood to include the G protein-coupled CXC chemokine receptors (CXCRs), including: CXC chemokine receptor 1 (CXCR1), CXC chemokine receptor 2 (CXCR2), CXC chemokine receptor 3 (CXCR3), CXC chemokine receptor 4 (CXCR4), CXC chemokine receptor 5 (CXCR5), CXC chemokine receptor 6 (CXCR6) and CXC chemokine receptor 7 (CXCR7). The phrase "chemokine receptor" is to be further understood to include the G protein-coupled XC chemokine receptor 1 (XCR1). The phrase "chemokine receptor" is to be further understood to include the G protein-coupled CX3 chemokine receptor ($CX_3CR1$). The phrase "chemokine receptor" is to be further understood to include the G protein-coupled CCX-CKR chemokine receptor (CCX-CKR). The phrase "chemokine receptor" is to be further understood to include the G protein-coupled D6 chemokine receptor (D6). The phrase "chemokine receptor" is to be further understood to include the G protein-coupled DARC/Duffy chemokine receptor (DARC). This list of chemokine receptors is compiled from a review by Allen (Allen, S. et al. (2007) Chemokine: Receptor Structure, Interactions and Antagonism. *Annual Review Immunology* 25:787-820). Finally, the phrase "chemokine receptor" is to be further understood to include any newly discovered CCR/CXCR/XCR/$CX_3$CR/CCX-CKR/D6/DARC family members.

The chemokine receptor may be selected from the group comprising the CC chemokine receptor 1 (CCR1), CC chemokine receptor 2 (CCR2), CC chemokine receptor 3 (CCR3), CC chemokine receptor 4 (CCR4), CC chemokine receptor 5 (CCR5), CC chemokine receptor 6 (CCR6), CC chemokine receptor 7 (CCR7), CC chemokine receptor 8 (CCR8), CC chemokine receptor 9 (CCR9), CC chemokine receptor 10 (CCR10), CXC chemokine receptor 1 (CXCR1), CXC chemokine receptor 2 (CXCR2), CXC chemokine receptor 3 (CXCR3), CXC chemokine receptor 4 (CXCR4), CXC chemokine receptor 5 (CXCR5), CXC chemokine receptor 6 (CXCR6) and CXC chemokine receptor 7 (CXCR7), the G protein-coupled XC chemokine receptor 1 (XCR1), the G protein-coupled CX3 chemokine receptor ($CX_3CR1$), the G protein-coupled CCX-CKR chemokine receptor (CCX-CKR), the G protein-coupled D6 chemokine receptor (D6), the G protein-coupled DARC/Duffy chemokine receptor (DARC), and a CCR/CXCR/XCR/$CX_3$CR/CCX-CKR/D6/DARC chemokine receptor.

The phrase "chemokine receptor pathway" is to be understood to at least include any one of the pathways triggered by the chemokine receptors listed above. Preferably, the chemokine receptor pathway is a pathway triggered by the G protein-coupled CC chemokine receptors (CCRs), including CC chemokine receptor 2 (CCR2).

The term "a component of the chemokine receptor pathway other than the chemokine receptor" as used herein, is to be understood as including a component of any one of the pathways listed above which is triggered by one or more of the chemokine receptors listed above, wherein the component is itself not a chemokine receptor as listed above. Preferably, the component is a protein such as, but not limited to, a transduction or signalling protein. The component of the chemokine receptor pathway may interact directly with the triggering chemokine receptor. Alternatively, the component of the chemokine receptor pathway may interact indirectly with the triggering chemokine receptor by way of protein-protein interaction or complex formation. Alternatively, the component of the chemokine receptor pathway may interact indirectly with the triggering chemokine receptor by way of a signalling cascade such as is known in the art.

The phrase "chemokine receptor pathway inhibitor" is intended to include any compound or agent which inhibits or partially inhibits any one of the pathways associated with the chemokine receptors listed above, including compounds or agents which inhibit components of the chemokine receptor pathway other than the chemokine receptor itself. For example, the inhibitor may inhibit or partially inhibit proteins that associate with chemokine receptors, or may inhibit compounds or pathway steps before and/or after the chemokine receptor itself. Preferably, the chemokine receptor pathway inhibitor is a CCR2 antagonist, CCR2 inverse agonist or CCR2 negative allosteric modulator.

The chemokine receptor pathway inhibitor may be selected from the group comprising a direct CCR2 antagonist, an inverse CCR2 agonist, a negative allosteric CCR2 modulator; an indirect CCR2 antagonist, an indirect inverse CCR2 agonist, and an indirect negative allosteric CCR2 modulator.

More preferably the phrase includes any inhibitor which inhibits or partially inhibits any one of the chemokine receptor pathways associated with MCP-1 and/or CCR2, which includes a direct CCR2 and/or MCP-1 antagonist, inverse agonist or negative allosteric modulator; or an antagonist, inverse agonist or negative allosteric modulator which works indirectly through blocking of these pathways at different levels.

More specifically, the phrase includes Propagermanium (3-oxygermylpropionic acid polymer), a molecule that has been used as a therapeutic agent against chronic hepatitis, also has been shown to specifically inhibit in vitro chemotactic migration of monocytes by MCP-1 through a mechanism that seems to require glycosylphosphatidylinositol (GPI)-anchored proteins such as CD55, CD59 and CD16 (Yokochi, S. (2001) Journal of Interferon and Cytokine Research 21:389-398). Propagermanium is also known as 3-[(2-Carboxyethyl-oxogermyl)oxy-oxogermyl]propanoic acid, proxigermanium, Ge-132, bis (2-carboxyethylgermanium) sesquioxide (CEGS), 2-carboxyethylgermasesquioxane, SK-818, organic germanium, germanium sesquioxide, 3,3'-(1,3-dioxo-1,3-digermanoxanediyl) bispropionic acid, 3-oxygermylpropionic acid polymer, poly-trans-(2-carboxyethyl) germasesquioxane, proxigermanium, repagermanium and Serocion. Propagermanium has the following formula:

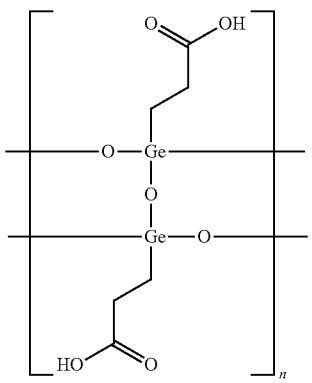

The phrase also includes RS504393. RS504393 has the following formula:

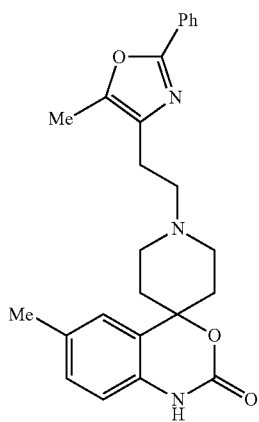 [SMILES: Cc1ccc2c(c1)C1(CCN(CCc3nc(-c4ccccc4)oc3C)CC1)OC(=O)N2]

The invention therefore also provides a pharmaceutical composition comprising:
a) at least one angiotensin receptor blocker or a pharmaceutically acceptable salt thereof; and
b) at least one chemokine receptor pathway inhibitor or a pharmaceutically acceptable salt thereof which inhibits a component of the chemokine receptor pathway other than the chemokine receptor.

The pharmaceutical composition may optionally further comprise a pharmaceutically acceptable carrier.

In one preferred embodiment the chemokine receptor pathway inhibitor is selected from the group consisting of:
(i) antagonists of chemokine receptors or components of the chemokine receptor pathway other than the chemokine receptor;
(ii) inverse agonists of chemokine receptors or components of the chemokine receptor pathway other than the chemokine receptor;
(iii) negative allosteric modulators of chemokine receptors or components of the chemokine receptor pathway other than the chemokine receptor;

A more specific example of a chemokine receptor pathway inhibitor which targets a component of the chemokine receptor pathway other than the chemokine receptor might be an agent which blocks pathways associated with MCP-1 induced migration, activation of monocytes and chemotactic migration. Such agents that might be targeted include glycosylphosphatidylinositol (GPI)-anchored proteins, and more specifically CD55, CD59 and CD16.

Known antagonists of chemokine receptors include; RS504393, RS102895, MLN-1202 (Millennium Pharmaceuticals), INCB3344, INCB3284 and INCB8696 (Incyte Pharmaceuticals), MK-0812 (Merck), CCX140 (ChemoCentryx), PF-4136309 (Pfizer), BMS-741672 (Bristol-Myers Squibb); Repertaxin (CXCR2), TAK-779 (CCR5), TAK-220 (CCR5), TAK-652 (CCR5), AK692 (CCR5), CMPD167 (CCR5), BX-471 (CCR1), AMD3100 (CXCR4), AMD11070 (CXCR4), FC131 (CXCR4), MLN3897 (CCR1), CP-481715 (CCR1), GW-873140 (CCR5). The chemokine receptor pathway inhibitor may be selected from the group comprising RS504393, RS102895, MLN-1202, INCB8696, MK-0812, CCX140, PF-4136309, BMS-741672; Repertaxin (CXCR2), TAK-779 (CCR5), TAK-220 (CCR5), TAK-652 (CCR5), AK692 (CCR5), CMPD167 (CCR5), BX-471 (CCR1), AMD3100 (CXCR4), AMD11070 (CXCR4), FC131 (CXCR4), MLN3897 (CCR1), CP-481715 (CCR1), and GW-873140 (CCR5).

In one preferred embodiment the chemokine receptor pathway inhibitor is an antagonist of a chemokine receptor. In one preferred embodiment the chemokine receptor pathway inhibitor is selected from the group consisting of: RS504393, RS102895, MLN-1202 (Millennium Pharmaceuticals), INCB3344, INCB3284, INCB8696 (Incyte Pharmaceuticals), MK-0812 (Merck), CCX140 (ChemoCentryx), PF-4136309 (Pfizer), BMS-741672 (Bristol-Myers Squibb); Repertaxin (CXCR2), TAK-779 (CCR5), TAK-220 (CCR5), TAK-652 (CCR5), AK692 (CCR5), CMPD167 (CCR5), BX-471 (CCR1), AMD3100 (CXCR4), AMD11070 (CXCR4), FC131 (CXCR4), MLN3897 (CCR1), CP-481715 (CCR1) and GW-873140 (CCR5). In one preferred embodiment the chemokine receptor pathway inhibitor is not RS102895.

In one preferred embodiment the chemokine receptor pathway inhibitor is propagermanium (also known as bis (2-carboxyethylgermanium) sesquioxide (CEGS), organic germanium, germanium sesquioxide, 3,3'-(1,3-dioxo-1,3-digermanoxanediyl) bispropionic acid, 3-oxygermylpropionic acid polymer, poly-trans-(2-carboxyethyl) germasesquioxane, proxigermanium, repagermanium and Serocion).

In one preferred embodiment the chemokine receptor pathway inhibitor inhibits the in vitro chemotactic migration of monocytes induced by MCP-1. In another preferred embodiment the chemokine receptor pathway inhibitor inhibits the in vitro chemotactic migration of monocytes induced by MCP-1 through a mechanism requiring glycosylphosphatidylinositol (GPI)-anchored proteins such as CD55, CD59 and CD16. In another preferred embodiment the chemokine receptor pathway inhibitor stabilizes the complexes CCR2/CD55 and/or CCR2/CD59 and/or CCR2/CD16. The chemokine receptor pathway inhibitor may be a peptide, polypeptide or small chemical entity. For example, the chemokine receptor pathway inhibitor may be a protein, binding protein or antibody.

The chemokine receptor pathway inhibitor may inhibit MCP-1 induced migration and activation of monocytes and chemotactic migration through the targeting of one or more glycosylphosphatidylinositol (GPI)-anchored proteins selected from the group comprising CD55, CD59 and CD16. The chemokine receptor pathway inhibitor may stabilize the complexes CCR2/CD55 and/or CCR2/CD59 and/or CCR2/CD16.

Propagermanium is a chemokine receptor pathway inhibitor, but it does not inhibit MCP-1 binding and appears to target glycosylphosphatidylinositol (GPI)-anchored proteins such as CD55, CD59 and CD16. (Yokochi (2001) Journal of Interferon and Cytokine Research 21:389-398; Yamada (2004) The Journal of Immunology 172: 3869-3875). Propagermanium inhibits in-vitro chemotactic migration of monocytes by MCP-1 (Yokuchi (2001) Journal of Interferon and Cytokine Research 21:389-398).

The invention provides a pharmaceutical composition comprising:
  a) at least one angiotensin receptor blocker or a pharmaceutically acceptable salt thereof; and
  b) propagermanium or a pharmaceutically acceptable salt thereof.

The invention provides a pharmaceutical composition comprising:
  a) at least one angiotensin receptor blocker or a pharmaceutically acceptable salt thereof; and
  b) RS504393, or a pharmaceutically acceptable salt thereof.

Key complement regulators CD55 (decay-accelerating factor) and CD59 (protectin) are both GPI-anchored plasma membrane proteins (Yokochi (2001) Journal of Interferon and Cytokine Research 21:389-398; Yamada (2004) The Journal of Immunology 172: 3869-3875). Defective regulation of complement inhibitors and reduced levels of CD55 and CD59 have been shown in a number of disease states including:
  i) kidney diseases and renal ischemia reperfusion injury (Yamada (2004) Critical Protection from Renal Ishemia Reperfusion Injury by CD55 and CD59, The Journal of Immunology 172: 3869-3875);
  ii) diabetes, where defective regulation of complement inhibitors and reduced levels of CD55 and CD59 may be viewed as a primary effect of diabetes and one of the mechanisms for complement activation in diabetic vessels with the selective decrease in these GPI-anchored complement inhibitors suggesting effects of diabetes on common regulatory steps in the synthesis or the processing of these molecules. It has been proposed that the mechanism that leads to decreased levels of CD59 and CD55 in diabetes may be cell- or tissue-specific. (Zhang (2002) Diabetes 51:3499-3504).
  iii) macrovascular diseases (Ma (2009) Chinese medical journal, 122(18) 2123-2128);
  iv) macular degeneration (Bora (2007) The Journal of Immunology, 178 (3) 1783-1790; and Ma K (2010) Invest Ophthalmol Vis Sci. December; 51(12):6776-83. Epub 2010 August)

The phrase "angiotensin receptor" or "ATR" is to be understood to mean either angiotensin receptor 1 (AT1R; $AT_1R$) or angiotensin receptor 2 (AT2R; $AT_2R$), being G protein-coupled receptors. In one preferred embodiment, they are analogous to those described by Porrello et al. (Porrello, E. R. et al (2009) Frontiers in Bioscience, 14:958-972), which are activated by angiotensin II (AngII) and/or angiotensin III (AngIII). "Angiotensin receptor" or "ATR" is to be further understood to include newly discovered angiotensin receptor family members.

The phrase "angiotensin receptor blocker" is understood to mean an agent or compound which can inhibit or partially inhibits the activation of the ATR. This includes antagonists for ATR, inverse agonists and negative allosteric modulators. Preferably, the angiotensin receptor blocker blocks AT1R.

The term "inhibits", as used herein, means a reduction below detectable limits when compared to a reference. The phrase includes blocking, retarding, or impeding an action to prevent an undesirable result.

The term "partially inhibits" as used herein, means any reduction within detectable limits when compared to a reference. The phrase includes blocking, retarding, or impeding an action to prevent an undesirable result.

The inhibition or partial inhibition may be measured using the in vitro methods set out herein, and include but are not limited to, biochemical or cellular assays for the assessment of in vitro chemotactic migration of monocytes by MCP-1 such as are known in the art, as well as measurement of inositol phosphate production, extracellular-regulated kinase (ERK) phosphorylation, cAMP production, label-free technologies (such as using impedance, light refraction or charge redistribution), G protein coupling using proximity reporter systems or other approaches, β-arrestin recruitment or mediated signalling, transcription factor-based reporter systems, microscopy visualization using fluorescent labels, use of antibodies to assess receptor cellular localization (such as enzyme-linked immunosorbent assays) and fluorescence activated cell sorting.

The inhibition or partial inhibition may be measured using the in vivo methods set out herein, and include but are not limited to, serial measurements of renal function made by the measurement of plasma creatinine and urea such as by way of an autoanalyser; the measurement of proteinuria, the measurement of albuminuria such as by way of a radioimmunoassay; and GFR (single shot isotopic technique); the assessment of endpoints such as renal and/or cardiac and/or ocular structure, by way of, for example, light microscopy (LM) for the assessment of glomerular and cardiac hypertrophy, glomerulosclerosis and/or fibrosis and/or podocyte change and/or; immunohistochemistry to measure the extent of matrix deposition and modulation of profibrotic growth factors and their activity; assessment of systolic blood pressure, modulation of insulin fasting plasma glucose, modulation of Hemoglobin A1c; and molecular biological techniques to assess renal and cardiac and ocular structure according to conventional assays such as known in the art. Inhibition or partial inhibition may be indicated by a qualitative improvement in renal and/or cardiac and/or ocular structure as measured by one or more of the above mentioned endpoints.

The term "component" as used herein in the context of a pharmaceutical composition of the invention, means either the angiotensin receptor blocker or the chemokine receptor pathway inhibitor.

In one preferred embodiment the angiotensin receptor blocker is selected from the group consisting of:
a) an angiotensin receptor antagonist;
b) an angiotensin receptor inverse agonist; or
c) an angiotensin receptor negative allosteric modulator.

In a further preferred embodiment the angiotensin receptor blocker is selected from the group consisting of: CGP-42112A (AT$_2$R antagonist; Sigma #C-160), Eprosartan (AT$_1$R; market name Teveten®, Abbott Laboratories USA), Losartan (AT$_1$R; market name Cozaar®, Merck & Co), Valsartan (AT$_1$R; market name Diovan®, Novartis), Telmisartan (AT$_1$R, market name Micardis®, Boehringer Ingelheim), Irbesartan (AT$_1$R, market name Avapro®, SanofiAventis), Candesartan (AT$_1$R, market name Atacand®, AstraZenica), Olmesartan (AT$_1$R, market name Benicar®, Daiichi Sankyo Inc), PD123319 (AT$_2$R, Tocris), ZD-7115 (AT$_1$R), Saralasin ((Sar$^1$-Ala$^8$)AngII), Sarthran ((Sar$^1$-Thr$^8$) AngII) and DuP753 (AT$_1$R). As an example, the angiotensin receptor blocker may be irbesartan. The angiotensin receptor blocker may be selected from the group comprising CGP-42112A (AT$_2$R antagonist), Eprosartan (AT$_1$R), Losartan (AT$_1$R), Valsartan (AT$_1$R), Telmisartan (AT$_1$R), Irbesartan (AT$_1$R), Candesartan (AT$_1$R), Olmesartan (AT$_1$R), PD123319 (AT$_2$R), ZD-7115 (AT$_1$R), Saralasin ((Sar$^1$-Ala$^8$) AngII), Sarthran ((Sar$^1$-Thr$^8$)AngII) and DuP753 (AT$_1$R).

Irbesartan is an Angiotensin II receptor antagonist also known as 2-butyl-3-({4-[2-(2H-1,2,3,4-tetrazol-5-yl)phenyl]phenyl}methyl)-1,3-diazaspiro[4.4]non-1-en-4-one. Irbesartan has the following formula:

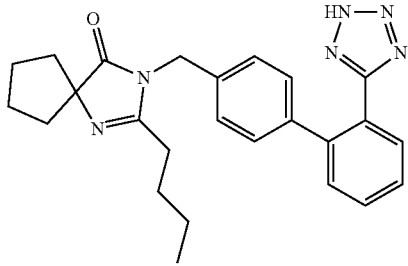 [SMILES: CCCCC1=NC2(CCCC2)C(=O)N1Cc1ccc(-c2ccccc2-c2nn[nH]n2)cc1]

In one preferred embodiment the angiotensin receptor blocker is not Olmesartan. In another preferred embodiment the angiotensin receptor blocker is not Olmesartan and the chemokine receptor pathway inhibitor is not RS102895. In another preferred embodiment the angiotensin receptor blocker is Olmesartan and the chemokine receptor pathway inhibitor is Propagermanium. In another preferred embodiment the angiotensin receptor blocker is Olmesartan and the chemokine receptor pathway inhibitor is a chemokine receptor pathway inhibitor which targets a component of the chemokine receptor pathway other than the chemokine receptor.

Olmesartan is an Angiotensin II receptor antagonist also known as (5-methyl-2-oxo-2H-1,3-dioxol-4-yl)methyl4-(2-hydroxypropan-2-yl)-2-propyl-1-({4-[2-(2H-1,2,3,4-tetrazol-5-yl)phenyl]phenyl}methyl)-1H-imidazole-5-carboxylate.

Olmesartan has the following formula:

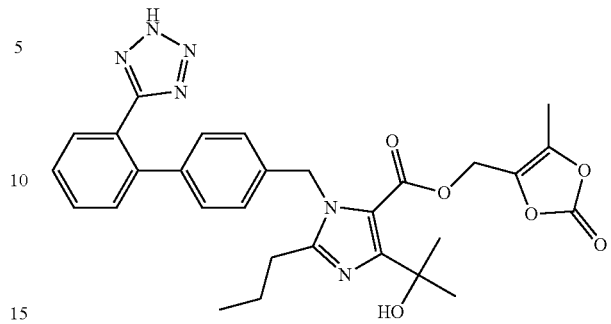

The invention therefore also provides a pharmaceutical composition comprising:
a) Olmesartan or a pharmaceutically acceptable salt thereof; and
b) at least one chemokine receptor pathway inhibitor or a pharmaceutically acceptable salt thereof which inhibits a component of the chemokine receptor pathway other than the chemokine receptor.

The invention therefore also provides a pharmaceutical composition comprising:
a) at least one angiotensin receptor blocker or a pharmaceutically acceptable salt thereof; and
b) propagermanium or a pharmaceutically acceptable salt thereof.

The invention therefore also provides a pharmaceutical composition comprising:
a) Olmesartan or a pharmaceutically acceptable salt thereof; and
b) propagermanium or a pharmaceutically acceptable salt thereof.

The invention therefore also provides a pharmaceutical composition comprising:
a) irbesartan or a pharmaceutically acceptable salt thereof; and
b) at least one chemokine receptor pathway inhibitor or a pharmaceutically acceptable salt thereof.

The invention further provides a pharmaceutical composition comprising:
a) irbesartan or a pharmaceutically acceptable salt thereof; and
b) RS504393, or a pharmaceutically acceptable salt thereof.

The invention further provides a pharmaceutical composition comprising:
a) irbesartan or a pharmaceutically acceptable salt thereof; and
b) at least one chemokine receptor pathway inhibitor or a pharmaceutically acceptable salt thereof which inhibits a component of the chemokine receptor pathway other than the chemokine receptor.

In one preferred embodiment, the total efficacy of the pharmaceutical composition is greater when compared to the efficacies of the angiotensin receptor blocker or the chemokine receptor pathway inhibitor when either component is administered without any administration of the other component. Thus, the combined composition may be administered in a single dose, including at sub-therapeutic doses, or less often, than either of the two components might be administered as single compounds.

Preferably, the total efficacy of the pharmaceutical composition is greater when compared to the sum of the efficacies of the angiotensin receptor blocker and the chemokine receptor pathway inhibitor when either component is administered without any administration of the other component. More preferably, a synergistic effect in efficacy is observed when the angiotensin receptor blocker and the chemokine receptor pathway inhibitor are administered concurrently or sequentially.

Alternatively, the total efficacy of the pharmaceutical composition is equal to the sum of the efficacies of the angiotensin receptor blocker and the chemokine receptor pathway inhibitor when either component is administered without any administration of the other component. As a further preferred embodiment of this alternative, an additive effect in efficacy is observed when the angiotensin receptor blocker and the chemokine receptor pathway inhibitor are administered concurrently or sequentially.

In a further alternative, the total efficacy of the pharmaceutical composition is less than the sum of the efficacies of the angiotensin receptor blocker and the chemokine receptor pathway inhibitor when either component is administered without any administration of the other component. In a further embodiment, while the combined efficacy is less than the sum of the efficacies of the angiotensin receptor blocker and the chemokine receptor pathway inhibitor when each component is administered without any administration of the other component, the treatment provides greater efficacy compared to a single treatment of angiotensin receptor blocker or the chemokine receptor pathway inhibitor administered alone.

Preferably the two components are administered concurrently at the same time (for example as two tablets taken together, or as a single tablet, formulated with each component) or sequentially (for example one tablet taken after another tablet). The doses of each component may be taken together (concurrently), or sequentially and taken within seconds, minutes, days, weeks or months of each other.

Method of Treatment

The present invention further provides a method for the treatment, amelioration or prevention of a condition or disease comprising administering to said subject a therapeutically effective amount of combination of (i) an angiotensin receptor blocker and (ii) an inhibitor of the chemokine receptor or its downstream pathways (a chemokine receptor pathway inhibitor).

The inhibitor of the chemokine receptor or its downstream pathways (the chemokine receptor pathway inhibitor) and the angiotensin receptor blocker used in the method of the present invention may be chosen from those discussed above.

Preferably, the condition or disease to be treated or prevented is a kidney disease, more particularly a disease selected from the group consisting of: fibrotic disorders in the kidney, chronic kidney disease caused by diabetic nephropathy, renal insufficiency (diabetic and non-diabetic), and renal failure conditions, including diabetic nephropathy, glomerulonephritis, scleroderma, glomerular sclerosis, proteinuria of primary renal disease and renal vascular hypertension.

The method of the invention may also be used to treat or prevent a condition selected from the group consisting of: cardiovascular disease including, (acute and chronic) congestive heart failure, left ventricular dysfunction and hypertrophic cardiomyopathy, diabetic cardiac myopathy, supraventricular and ventricular arrhythmias, atrial fibrillation or atrial flutter, myocardial infarction and its sequelae, atherosclerosis, angina (whether unstable or stable), heart failure, angina pectoris, diabetes, secondary aldosteronism, primary and secondary pulmonary hyperaldosteronism, primary and pulmonary hypertension, diabetic retinopathy, macular degeneration, ocular disorders, insulin resistance, the management of other vascular disorders, such as migraine, Raynaud's disease, luminal hyperplasia, cognitive dysfunction (such as Alzheimer's), stroke, hyperkalemia, preeclampsia, sarcoidosis, HIV infection and AIDS pathogenesis, ischemia and reperfusion injury, atherogenesis, chronic obstructive pulmonary disease, asthma and allergy renal disease, rheumatoid arthritis.

Generally, a range of ailments which are chemokine-related may be treated by the method of the present invention, including ailments that are related to increased or decreased production of chemokines, and/or increased or decreased responsiveness of cells to chemokines. A chemokine-related ailment should also be understood to mean a condition in which chemokine receptors display aberrant characteristics, are the target of a particular pathogen or are a target of a pharmacological intervention. The following list provides some examples of chemokine-related ailments:

HIV infection and AIDS pathogenesis
Ischemia and reperfusion injury;
Atherogenesis;
Chronic obstructive pulmonary disease;
Asthma and allergy;
Renal disease
Rheumatoid arthritis However, it should be understood that the phrase 'chemokine-related interventions' and the phrase 'a chemokine-related ailment' is not limited thereto.

A range of ailments which are related to angiotensin may also be treated by the method of the present invention, including ailments that are related to increased or decreased production of angiotensin, and/or increased or decreased responsiveness of cells to angiotensin. Listed below are a number of conditions that have either been proposed to stem from a dysregulated angiotensin system, or, could potentially be treated using angiotensin-based interventions:

Chronic heart failure;
Atherosclerosis/ischemia;
Hypertension;
Hyperkalemia;
Preeclampsia;
Diabetes mellitus;
Diabetic retinopathy;
Sarcoidosis;
Alzheimer's Disease The condition or disease to be treated or prevented may be a disease selected from the group comprising fibrotic disorders in the kidney, chronic kidney disease caused by diabetic nephropathy, renal insufficiency, renal failure conditions, diabetic nephropathy, glomerulonephritis, scleroderma, glomerular sclerosis, proteinuria of primary renal disease, renal vascular hypertension, cardiovascular disease, chronic heart failure, hypertension, congestive heart failure, left ventricular dysfunction, hypertrophic cardiomyopathy, diabetic cardiac myopathy, supraventricular and ventricular arrhythmias, atrial fibrillation, atrial flutter, myocardial infarction and its sequelae, atherosclerosis, angina, heart failure, angina pectoris, secondary aldosteronism, primary and secondary pulmonary hyperaldosteronism, primary and pulmonary hypertension, diabetic retinopathy, macular degeneration, ocular disorders, insulin resistance, the vascular disorders, migraine, Raynaud's disease, luminal hyperplasia, cognitive dysfunction, Alzheimer's disease, stroke, hyperkalemia, preeclampsia, sarcoidosis, Diabetes mellitus; Diabetic retinopathy, HIV infection, AIDS pathogenesis, ischemia and reperfusion injury, atherogenesis, chronic obstructive pulmonary disease, asthma, allergy renal disease, and rheumatoid arthritis.

In one aspect, the chemokine receptor pathway inhibitor inhibits or partially inhibits a protein other than the chemokine receptor, more preferably, the inhibitor is an agent which blocks MCP-1 induced migration and activation of monocytes and chemotactic migration through the targeting of glycosylphosphatidylinositol (GPI)-anchored proteins such as CD55, CD59 and CD16. Most preferably, the chemokine receptor pathway inhibitor is propagermanium.

While not intending to be restricted to any particular mode of action, in one preferred embodiment the chemokine receptor inhibitor has a greater affinity and/or potency and/or efficacy when interacting with the chemokine receptor or modulating its downstream pathways when the chemokine receptor is associated with the angiotensin receptor. For example, the chemokine receptor and the angiotensin receptor may be associated as a chemokine receptor/angiotensin receptor hetero-dimer/-oligomer. In a further preferred embodiment, when the chemokine receptor inhibitor is administered to a subject concurrently or sequentially with an angiotensin receptor blocker, the combined affinity, potency and/or efficacy is greater than compared to the affinity, potency and/or efficacy that would have been achieved when the chemokine receptor inhibitor is not administered in combination (whether concurrently or sequentially) with the angiotensin receptor blocker. In an even further preferred embodiment, a synergistic effect (as measured by affinity, potency and/or efficacy) is achieved when the chemokine receptor inhibitor is administered to a subject in combination (whether concurrently or sequentially) with an angiotensin receptor blocker.

While not intending to be restricted to any particular mode of action, in one preferred embodiment the angiotensin receptor blocker has a greater affinity and/or potency and/or efficacy when interacting with the angiotensin receptor when the angiotensin receptor is associated with the chemokine receptor. For example, the chemokine receptor and the angiotensin receptor may be associated as a chemokine receptor/angiotensin receptor hetero-dimer/-oligomer. In a further preferred embodiment, when the angiotensin receptor blocker is administered to a subject concurrently or sequentially with a chemokine receptor inhibitor, the combined affinity, potency and/or efficacy is greater than compared to the affinity, potency and/or efficacy that would have been achieved when the angiotensin receptor blocker is not administered in combination (whether concurrently or sequentially) with the chemokine receptor inhibitor. In an even further preferred embodiment, a synergistic effect (as measured by affinity, potency and/or efficacy) is achieved when the angiotensin receptor blocker is administered to a subject in combination (whether concurrently or sequentially) with a chemokine receptor inhibitor.

Manufacture of a Medicament

The invention also provides for the use of a pharmaceutical composition comprising at least one angiotensin receptor blocker or a pharmaceutically acceptable salt thereof, and at least one chemokine receptor pathway inhibitor or a pharmaceutically acceptable salt thereof; for the manufacture of a dosage form for the treatment of a disease. The pharmaceutical composition may optionally further comprise a pharmaceutically acceptable carrier.

Dosage Forms, Formulations and Administration

The dosage form provided by the present invention may further comprise a vial, cartridge, container, tablet or capsule comprising the pharmaceutical composition of the invention together with dosage instructions for the administration of the dosage form to a subject for the treatment, amelioration or prevention of a disease.

Dosage levels of the compounds of the invention will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of each active ingredient which may be combined with the carrier materials to produce a single dosage will vary, depending upon the host to be treated and the particular mode of administration. For example, a formulation intended for oral administration to humans may contain about 5 mg to 1 g of each active compound with an appropriate and convenient amount of carrier material, which may vary from about 5 to 95 percent of the total composition. Dosage unit forms will generally contain between from about 5 mg to 500 mg of active ingredient.

Preferably, the angiotensin receptor blocker is provided at a dose of between 50 mg to 500 mg per day. Even more preferably, the chemokine receptor pathway inhibitor is provided at a dose of between 150 mg to 300 mg per day. For example, the angiotensin receptor blocker is Irbesartan and is administered at a dose of 300 mg per day.

Preferably, the chemokine receptor pathway inhibitor is provided at a dose of between 5 mg to 2000 mg per day. Even more preferably the chemokine receptor pathway inhibitor is provided at a dose of between 5 mg to 50 mg per day. For example, the chemokine receptor pathway inhibitor is propagermanium and is provided at a dose of 30 mg per day.

The dosage form may comprise about 5 mg to 1 g of the angiotensin receptor blocker or a pharmaceutically acceptable salt thereof, and about 5 mg to 1 g of the chemokine receptor pathway inhibitor or a pharmaceutically acceptable salt thereof. The dosage form may comprise a daily dose of angiotensin receptor blocker of between about 50 mg to 500 mg. The angiotensin receptor blocker may be Irbesartan, and the dosage form may comprise a daily dose of Irbesartan of about 300 mg. The dosage form may also comprise a daily dose of chemokine receptor pathway inhibitor of between about 5 mg to 50 mg. The chemokine receptor pathway inhibitor may be propagermanium and the dosage form may comprise a daily dose of propagermanium of about 30 mg It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Medicaments of the invention, in various aspects, may be administered by injection, or prepared for oral, pulmonary, nasal or for any other form of administration. Preferably the medicaments are administered, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally or by aerosol administration.

The mode of administration is in one aspect at least suitable for the form in which the medicament has been prepared. The mode of administration for the most effective response is in one aspect determined empirically and the means of administration described below are given as examples, and do not limit the method of delivery of the composition of the present invention in any way. All the above formulations are commonly used in the pharmaceutical industry and are commonly known to suitably qualified practitioners.

The medicaments of the invention in certain aspects may include pharmaceutically acceptable nontoxic excipients and carriers and administered by any parenteral techniques such as subcutaneous, intravenous and intraperitoneal injections. In addition the formulations may optionally contain one or more adjuvants. As used herein, a "pharmaceutical carrier" is a pharmaceutically acceptable solvent, suspending agent, excipient or vehicle for delivering the compounds to the subject. The carrier may be liquid or solid, and is selected with the planned manner of administration in mind.

The pharmaceutical forms suitable for injectable use optionally include sterile aqueous solutions (where water-soluble) or dispersions and sterile powders for the extemporaneous preparation of sterile injectable solutions or dispersion. Alternatively, the compounds of the invention are, in certain aspects encapsulated in liposomes and delivered in injectable solutions to assist their transport across cell membrane. Alternatively or in addition such preparations contain constituents of self-assembling pore structures to facilitate transport across the cellular membrane. The carrier, in various aspects, is a solvent or dispersion medium containing, for example, water, ethanol, polyol (for example, glycerol, propylene glycol and liquid polyethylene glycol, and the like), suitable mixtures thereof, and vegetable oils. Proper fluidity is maintained, for example and without limitation, by the use of a coating such as lecithin, by the maintenance of the required particle size in the case of dispersion and by the use of surfactants. Prolonged absorption of the injectable compositions is in certain aspects brought about by the use in the compositions of agents delaying absorption, for example, aluminum monostearate and gelatin.

The invention also provides an injectable sustained release pharmaceutical composition comprising a therapeutically effective pharmaceutical composition according to the invention, and a release retardant. The release retardant may be, for example, aluminum monostearate and gelatin.

Sterile injectable solutions are prepared by incorporating the active compounds in the required amount in an appropriate solvent with various of the other ingredients enumerated above, as required, followed by filtered sterilisation. Generally, dispersions are prepared by incorporating the various sterilised active ingredient into a sterile vehicle that contains the basic dispersion medium and the required other ingredients from those enumerated above. In the case of sterile powders for the preparation of sterile injectable solutions, preparation in certain aspects include without limitation vacuum drying and freeze-drying techniques that yield a powder of the active ingredient plus any additional desired ingredient from previously sterile-filtered solution thereof.

Contemplated for use herein are oral solid dosage forms, which are described generally in Martin, Remington's Pharmaceutical Sciences, 18th Ed. (1990 Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatised with various polymers (E.g., U.S. Pat. No. 5,013,556). A description of possible solid dosage forms for the therapeutic is given by Marshall, in Modern Pharmaceutics, Chapter 10, Banker and Rhodes ed., (1979), herein incorporated by reference. In general, the formulation will include the compounds described as part of the invention (or a chemically modified form thereof), and inert ingredients which allow for protection against the stomach environment, and release of the biologically active material in the intestine.

For the chemokine receptor pathway inhibitor or angiotensin receptor blocker of the invention the location of release may be the stomach, the small intestine (the duodenum, the jejunum, or the ileum), or the large intestine. One skilled in the art has available formulations that will not dissolve in the stomach, yet will release the material in the duodenum or elsewhere in the intestine. In one aspect, the release will avoid the deleterious effects of the stomach environment, either by protection of the composition or by release of the compounds beyond the stomach environment, such as in the intestine.

The invention further provides an oral sustained release pharmaceutical composition comprising a therapeutically effective pharmaceutical composition according to the invention, and a release retardant.

In one aspect of the present invention the release retardant is a water-soluble, water swellable and/or water insoluble polymer. In particular, water-soluble polymers are selected from the group comprising are ethylcellulose, hydroxypropyl cellulose, hydroxypropyl methyl cellulose, an enteric coating; and a semipermeable membrane. In another aspect of the invention the release retardant is a non-polymeric release retardant. More particularly, the non-polymeric release retardant is hydrogenated castor oil. The compositions of the invention may be milled or granulated and compressed into tablets or encapsulated into capsules according to conventional procedures known in the art.

To ensure full gastric resistance, a coating impermeable to at least pH 5.0 is used. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This includes without limitation sugar coatings, or coatings that make the tablet easier to swallow. Exemplary capsules consist of a hard shell (such as gelatin) for delivery of dry therapeutic i.e. powder; for liquid forms, a soft gelatine shell may be used. The shell material of cachets in certain aspects is thick starch or other edible paper. For pills, lozenges, moulded tablets or tablet triturates, moist massing techniques are also contemplated, without limitation.

As used herein, the term "sustained release" means the gradual but continuous or sustained release over a relatively extended period of the therapeutic compound content after oral ingestion. The release may continue after the pharmaceutical composition has passed from the stomach and through until and after the pharmaceutical composition reaches the intestine. The phrase "sustained release" also means delayed release wherein release of the therapeutic compound is not immediately initiated upon the pharmaceutical composition reaching the stomach but rather is delayed for a period of time, for example, until when the pharmaceutical composition reaches the intestine. Upon reaching the intestine, the increase in pH may then trigger release of the therapeutic compound from the pharmaceutical composition.

Though term "release retardant" is used herein, means a substance that reduces the rate of release of a therapeutic compound from a pharmaceutical composition when orally ingested. The release retardant may be a polymer or a non-polymer. The release retardant may be used according to any one of several sustained release systems including, for example, a diffusion system, a dissolution system and/or an osmotic system.

In certain aspects, the therapeutic is included in the formulation as fine multiparticulates in the form of granules or pellets of particle size about 1 mm. The formulation of the material for capsule administration is, in certain aspects, a powder, lightly compressed plugs or even as tablets. In one aspect, the therapeutic could be prepared by compression.

Colourants and flavouring agents are optionally all be included. For example, compounds may be formulated (such as, and without limitation, by liposome or microsphere encapsulation) and then further contained within an edible product, such as a refrigerated beverage containing colorants and flavouring agents.

The volume of the therapeutics, in one aspect, diluted or increased with an inert material. These diluents could include carbohydrates, especially mannitol, alpha-lactose, anhydrous lactose, cellulose, sucrose, modified dextrans and starch. Certain inorganic salts are also optionally used as fillers including calcium triphosphate, magnesium carbonate and sodium chloride. Some commercially available diluents are Fast-Flo, Emdex, STA-Rx 1500, Emcompress and Avicell.

In other embodiments, disintegrants are included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatine, orange peel, acid carboxymethyl cellulose, natural sponge and bentonite are also contemplated. Another form of the disintegrants is the insoluble cationic exchange resins. Powdered gums are also optionally used as disintegrants and as binders and these include, without limitation, powdered gums such as agar, Karaya or tragacanth. Alginic acid and its sodium salt are also useful as disintegrants.

Binders are contemplated to hold the therapeutic compounds together to form a hard tablet and include, without limitation, materials from natural products such as acacia, tragacanth, starch and gelatin. Other binders include, without limitation, methylcellulose (MC), ethyl cellulose (EC) and carboxymethyl cellulose (CMC). Polyvinyl pyrrolidone (PVP) and hydroxypropylmethyl cellulose (HPMC) are contemplated for use in alcoholic solutions to granulate the therapeutic.

An antifrictional agent may be optionally included in the formulation of the therapeutic to prevent sticking during the formulation process. Lubricants may be optionally used as a layer between the therapeutic and the die wall, and these can include but are not limited to: stearic acid including its magnesium and calcium salts, polytetrafluoroethylene (PTFE), liquid paraffin, vegetable oils and waxes. Exemplary soluble lubricants may also be used such as include sodium lauryl sulfate, magnesium lauryl sulfate, polyethylene glycol of various molecular weights, and Carbowax 4000 and 6000.

Glidants that might improve the flow properties of the compound during formulation and to aid rearrangement during compression might be optionally added. The glidants may include without limitation starch, talc, pyrogenic silica and hydrated silicoaluminate.

To aid dissolution of the therapeutic into the aqueous environment, a surfactant might be added in certain embodiments as a wetting agent. Surfactants may include, for example and without limitation, anionic detergents such as sodium lauryl sulfate, dioctyl sodium sulfosuccinate and dioctyl sodium sulfonate. Cationic detergents might be optionally used and could include, without limitation, benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. When used, these surfactants could be present in the formulation of the compounds either alone or as a mixture in different ratios.

Additives which that potentially enhance uptake of the compounds are for instance and without limitation the fatty acids oleic acid, linoleic acid and linolenic acid.

Controlled release formulation may be desirable. The formulations are also contemplated. In certain aspects, the compounds could be incorporated into an inert matrix that permits release by either diffusion or leaching mechanisms i.e., gums. In some aspects, slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some enteric coatings also have a delayed release effect.

In other aspects, a mix of materials might be used to provide the optimum film coating. Film coating may be carried out, for example and without limitation, in a pan coater or in a fluidized bed or by compression coating.

Also contemplated herein is pulmonary delivery of the compounds. In these aspects, the compounds may be delivered to the lungs of a mammal while inhaling and traverses across the lung epithelial lining to the blood stream.

Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are, for example and without limitation, the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the compounds. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated.

Formulations suitable for use with a nebulizer, either jet or ultrasonic, will typically comprise the compounds suspended in water. The formulation may also include, in one aspect, a buffer and a simple sugar (e.g., for protein stabilization and regulation of osmotic pressure). In one embodiment, the nebulizer formulation may also contain a surfactant, to reduce or prevent surface induced aggregation of the compounds caused by atomization of the solution in forming the aerosol.

Formulations for use with a metered-dose inhaler device will generally comprise, in one aspect a finely divided powder containing the compounds suspended in a propellant with the aid of a surfactant. The propellant may be is any conventional material employed for this purpose, such as and without limitation, a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include, without limitation sorbitan trioleate and soya lecithin. Oleic acid may also be useful as a surfactant in certain aspects.

Formulations for dispensing from a powder inhaler device will comprise a finely divided dry powder containing the compound and may also include a bulking agent, such as and without limitation lactose, sorbitol, sucrose, or mannitol in amounts which facilitate dispersal of the powder from the device, e.g., 50 to 90% by weight of the formulation. In certain embodiments, the compound(s) is/are prepared in particulate form with an average particle size of less than 10 microns, most preferably 0.5 to 5 microns, for most effective delivery to the distal lung.

Nasal delivery of the compounds is also contemplated. Nasal delivery allows the passage of the protein to the blood stream directly after administering the therapeutic product to the nose, without the necessity for deposition of the product in the lung. Formulations for nasal delivery include those with, for example and without limitation, dextran or cydodextran.

It will be appreciated that in certain aspects, the medicaments of the invention may be given as a single dose schedule, or preferably, in a multiple dose schedule. A multiple dose schedule is one in which a primary course of delivery may be with 1 to 10 separate doses, is optionally followed by other doses given at subsequent time intervals required to maintain or reinforce the treatment. The dosage regimen will also, at least in part, be determined by the needs of the individual and the judgement of the practitioner.

The invention thus provides a tablet comprising the pharmaceutical composition of the invention; a capsule comprising the pharmaceutical composition of the invention and injectable suspension comprising the pharmaceutical composition of the invention, and a composition for pulmonary delivery comprising the pharmaceutical competition of the invention.

Assessing the Efficacy of the Pharmaceutical Compositions

In another aspect of the invention, there is provided a method for assessing the efficacy of a pharmaceutical composition of the invention, wherein the method includes a step selected from the group including: assessing the in vitro chemotactic migration of monocytes by MCP-1 by way of an in vitro biochemical or cellular assay; measuring inositol phosphate production, extracellular-regulated kinase (ERK) phosphorylation or cAMP production; measuring the effect of the composition using label-free technologies, such as using impedance, light refraction or charge redistribution; measuring G protein coupling using proximity reporter systems or other approaches; measuring β-arrestin recruitment or mediated signalling; measuring the effect of the composition using transcription factor-based reporter systems; utilizing in vitro biochemical or cellular techniques to measure cellular localization, such as microscopy visualization using fluorescent labels, use of antibodies (such as enzyme-linked immunosorbent assays) and fluorescence activated cell sorting; measuring the in vivo levels of plasma creatinine and urea, as indicative of renal function, such as by way of an autoanalyser; measuring the levels of proteinuria, measuring the levels of albuminuria by way of a radioimmunoassay; measuring GFR (single shot isotopic technique); assessing renal and/or cardiac and/or ocular or other tissue structure by way of light microscopy (LM); assessing the presence and/or extent of glomerular and/or cardiac hypertrophy, glomerulosclerosis and/or fibrosis; assessing the extent of matrix deposition, assessing the modulation of profibrotic growth factors and their activity; assessing renal and/or cardiac structure and/or ocular structure and/or other tissue structure; and assessing systolic blood pressure, modulation of insulin fasting plasma glucose, and/or modulation of Hemoglobin A1c.

In a further aspect of the invention, there is provided a method for assessing the inhibition or partial inhibition activity of a pharmaceutical composition of the invention, wherein the inhibition or partial inhibition is indicated by a qualitative improvement in renal and/or cardiac and/or ocular and/or other tissue structure as measured by one or more of the following: levels of plasma creatinine and urea; levels of proteinuria, levels of albuminuria; GFR (using single shot isotopic technique); integrity of renal and/or cardiac and/or ocular structure; the extent of matrix deposition; modulation of the activity of profibrotic growth factors; light microscopy (LM) for the assessment of glomerular and/or cardiac hypertrophy, glomerulosclerosis and/or fibrosis; immunohistochemistry to measure the extent of matrix deposition and modulation of profibrotic growth factors and their activity; and molecular biological techniques to assess renal and/or cardiac and/or ocular structure.

The invention will now be further described by way of reference only to the following non-limiting examples. It should be understood, however, that the examples following are illustrative only, and should not be taken in any way as a restriction on the generality of the invention described above.

EXAMPLES

Example 1—Reduction of Proteinuria in STNx Model (Low Dose Propagermanium)

Sub-Total Nephrectomy (STNx) Surgery

Animal

Six weeks old, male Sprague-Dawley (SD) rats weighing 200-250 g are sourced from Animal Resources Centre (Western Australia). The animal study is conducted with the approval from the Animal Ethics Committee (St Vincent's Hospital and the National Health and Medical Research Foundation of Australia). All rats receive normal rat chow (Certified Rodent Diet #5002, LabDiet, USA) and drinking water ad libitum. All animals are housed in a stable environment maintained at 22±1° C. with a 12-hour light/dark cycle commencing at 6 am. STNx surgery is performed in operating theater at St Vincent's Experimental Surgical Unit. All surgical procedures are modified from those previously described (Gilbert, R. E., L. L. Wu, et al. (1999). "Pathological expression of renin and angiotensin II in the renal tubule after subtotal nephrectomy. Implications for the pathogenesis of tubulointerstitial fibrosis." *Am J Pathol* 155(2): 429-40; Kelly, D. J., A. J. Edgley, et al. (2009). "Protein kinase C-beta inhibition attenuates the progression of nephropathy in non-diabetic kidney disease." *Nephrol Dial Transplant* 24(6): 1782-90; Kelly, D. J., C. Hepper, et al. (2003). "Vascular endothelial growth factor expression and glomerular endothelial cell loss in the remnant kidney model." *Nephrol Dial Transplant* 18(7): 1286-92; Wu, L., A. Cox, et al. (1997). "Transforming growth factor β1 and renal injury following subtotal nephrectomy in the rat: Role of the renin-angiotensin system." *Kidney Int* 51: 1553-1567.)

Pre-Operative Care

The afternoon before surgery, the rats are weighed and given one dose of antibiotics (oxytetracycline, 30 mg/kg) as prophylaxis by oral gavage. The rats are then fasted overnight.

Operative Care

Anaesthesia

Anaesthesia is induced with 2.5% isoflurane mixed with oxygen in a Perspex plastic box.

Once anaesthetized, the rat is then laid on its back on a heat pad (maintained at 37° C.), and a facemask is then placed over the rat's nose and mouth to deliver isoflurane, maintaining anaesthesia with 1-2% isoflurane/97% oxygen in a tidal volume of 1 ml/100 g body weight.

Skin Preparation

The abdominal area of the rat is shaved from the sternum to the pelvic area using clippers. The shaved area is cleaned 3 times with Chlorhexidine in Alcohol 70%, in a circular motion, starting at the incision point (midline) and cleaning outwards.

Surgery

A fenestrated drape is placed over the incision site and a skin incision is made from 10 mm below the sternum to 10 mm above the genitals with a No. 23 scalpel blade. The muscle layer is then exposed and raised with tissue forceps to allow for an incision along the linea alba (the fascia joining the muscle layers along the midline) to be made. This raising of the muscle layer prevents the intestines being accidentally damaged by sharp instruments.

Once a small hole is made in the muscle layer using a scalpel blade, fine scissors are used to complete the incision. With both incisions complete, gauze is placed over the drape surrounding the incision site and 0.9% saline is used to moisten the gauze. Using moistened cotton buds, the left kidney is located and raised onto the gauze. Under the microscope, toothed forceps and cotton buds are then used to dissect fat away from the renal pelvis exposing the branches of renal arteries just before into the kidney. Individual branches of renal arteries (3-4) are then isolated by blunt dissection using fine forceps. 4.0 silk is then passed under the arteries until enough arteries are isolated to incapacitate blood flow to ⅔ of the kidney, rendering this area dead. Once it is ascertained that there is no bleeding and ⅓ of the kidney is still functioning, the kidney is placed back into the abdomen.

The right kidney is then exposed and the renal capsule removed. 4.0 silk is used to tie off the kidney at the renal pelvis, ligating the whole kidney and the ureter. Three knots are tied on one side, the silk weaved to the other side and a further three knots tied on the other side. The kidney is then cut out. When it is ascertained that there is no bleeding, the vascular stump is placed back into the abdomen. The left kidney can then be re-checked to make sure the colour change is sufficient and the remaining ⅓ of the kidney is still functional. Both left and right ureters are checked without any damages, 2.0 mls of 0.9% saline is then placed into the abdomen to aid in re-hydrating the rat in case there was fluid loss while the cavity was open.

Wound Closure 5.0 dissolvable sutures (PGA—Polyglycolic Acid sutures) are then used to stitch the muscle layer in a continuous stitch. The skin is then stitched with a continuous stitch of 4.0 silk. The area is then cleaned with Chlorhexidine in Alcohol 70% to remove any blood from the skin. The anaesthetic mask is then removed and Op-site spray (tissue spray) is sprayed onto the incision site to add an extra barrier for protection against infection. While the rat is beginning to wake from anaesthesia, Buprenorphine (Temgesic) is given at a dose of 0.03 mg/kg subcutaneously.

Recovery Period

The rat is then allowed to recover on a heat pad maintained at 37° C.

Post-Operative Care

Post-operatively, a solution of 5% glucose is given in a drinking bottle alongside a water bottle in order to give the rats the option of drinking one or the other. Food is also placed in the bottom of the box to facilitate eating. 12 to 24 hours post-surgery, if the rat is not eating or drinking, buprenorphine is administered at subcutaneously. 24 to 48 hours post-surgery if the rat appears depressed, reluctant to move, or is in a hunched position, this may be the result of renal failure. In this case, the rats are culled using an overdose of pentobarbitone sodium (120 mg/kg ip).

Every 4 weeks, systolic blood pressure (SBP) will be determined in preheated conscious rats via tail-cuff plethysmography using a non-invasive blood pressure (NIBP) controller and Powerlab (AD instruments, NSW, Australia).

Sham Surgery

The control rats will undergo sham surgery consisting of laparotomy as described above and manipulation of both kidneys without dissecting renal arteries before wound closure.

Study Design and Procedures

Treatments start 14 days following surgery.

Long Term (12 Weeks)

Untreated Groups

Groups 1, 2 Untreated: Control, Diabetic

Single Agent Group

Group 3 STNx+Irbesartan (ARB) (10 mg/kg/day)

Combination Group

Group 4 STNx+Irbesartan (10 mg/kg/day)/Propagermanium (3 mg/kg/day)

n=16 rats per group

Clinical Parameters

Serial measurements of systolic blood pressure (SBP) and clinical parameters were undertaken at intervals as per standard protocols for animal studies (every 4 weeks) (Kelly D J, Wilkinson-Berka J L, T. J. A, et al.: A new model of progressive diabetic renal impairment in the transgenic (mRen-2)27 rat. *Kidney Int.* 54:343-352, 1998).

Renal and Cardiac Function (Primary Endpoints)

Serial measurements of renal function were made by the measurement of plasma creatinine and urea (autoanalyser), albuminuria (radioimmunoassay, every 4 weeks) and GFR (single shot isotopic technique, 4 and 12 weeks) as per standard protocols for animal studies (Kelly et al, 1998).

Future Experiments—Renal and Cardiac Structure (Secondary Endpoints)

Further experiments that could be performed include assessing secondary endpoints such as renal and cardiac structure. For example, light microscopy (LM) could be used to measure glomerular and cardiac hypertrophy, glomerulosclerosis and fibrosis. Immunohistochemistry could be used to measure the extent of matrix deposition and modulation of profibrotic growth factors and their activity. Molecular biology could also be used to assess renal and cardiac structure.

Statistical Considerations

Comparisons between animal groups were performed using an ANOVA with a Fishers post hoc test. The justification of animal usage has been calculated to be n=16 rats per group (n=8 for Histology, n=8 for molecular biology). Values of p<0.05 were considered statistically significant. Albuminuria was analysed following log transformation of data and geometric means x/÷ tolerance factors.

As shown in FIG. 1, improved levels of proteinurea were achieved in the sub-total nephrectomy (STNx) model of end organ renal disease when animals were treated with a combination of an angiotensin receptor blocker and a low dose of propagermanium (STNx+Irb+PPG) as compared to untreated STNx animals and animals treated with the angiotensin receptor blocker alone (STNx+Irb).

Example 2—Reduction of Proteinuria in STNx Model (High Dose Propagermanium)

As described for Example 1 but with the following treatments:

Study Design and Procedures

Treatments start 14 days following surgery.

Long Term (12 Weeks)

Untreated Groups

Groups 1, 2 Untreated: Control, Diabetic

Single Agent Group

Group 3 STNx+Irbesartan (ARB) (10 mg/kg/day) or STNx+ Propagermanium (30 mg/kg/day)

Combination Group

Group 4 STNx+Irbesartan (10 mg/kg/day)/Propagermanium (30 mg/kg/day)

n=16 rats per group

Figure 2:
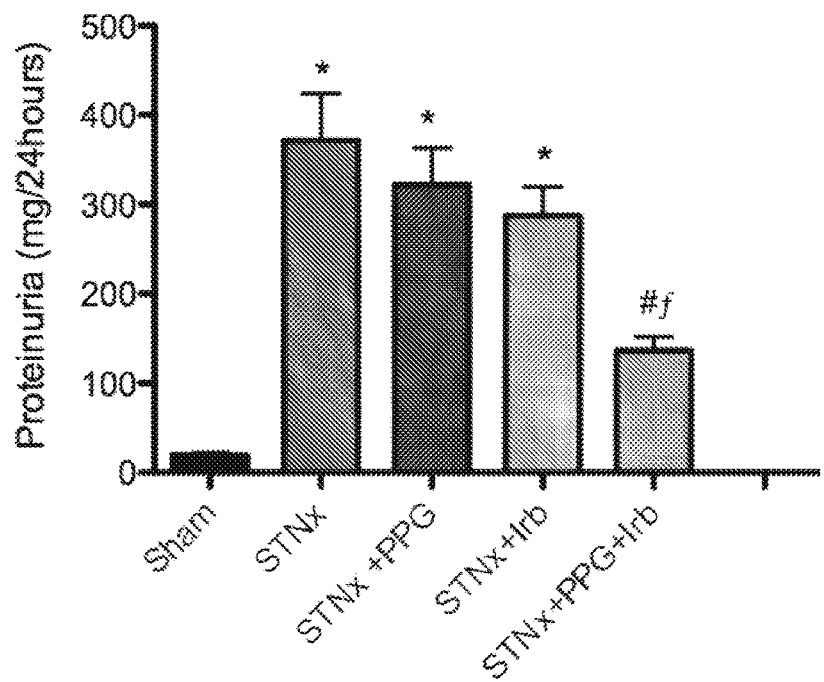
FIG. 2: shows a bar graph of the improvement in levels of proteinurea achieved in the sub-total nephrectomy (STNx) model of end organ renal disease when treated with a combination of Irbesartan (Irb), an angiotensin receptor blocker, and propagermanium (PPG) (a chemokine receptor pathway inhibitor) (high dose) as compared to untreated animals, animals treated with PPG alone, and animals treated with the angiotensin receptor blocker alone as described in Example 2.

As shown in FIG. 2, improved levels of proteinurea were achieved in the sub-total nephrectomy (STNx) model of end organ renal disease when animals were treated with a combination of an angiotensin receptor blocker and a high dose of propagermanium (STNx+PPG+Irb) as compared to untreated STNx animals, STNx animals treated with a high dose of propagermanium alone (STNx+PPG), and STNx animals treated with the angiotensin receptor blocker alone (STNx+Irb).

Figure 3:
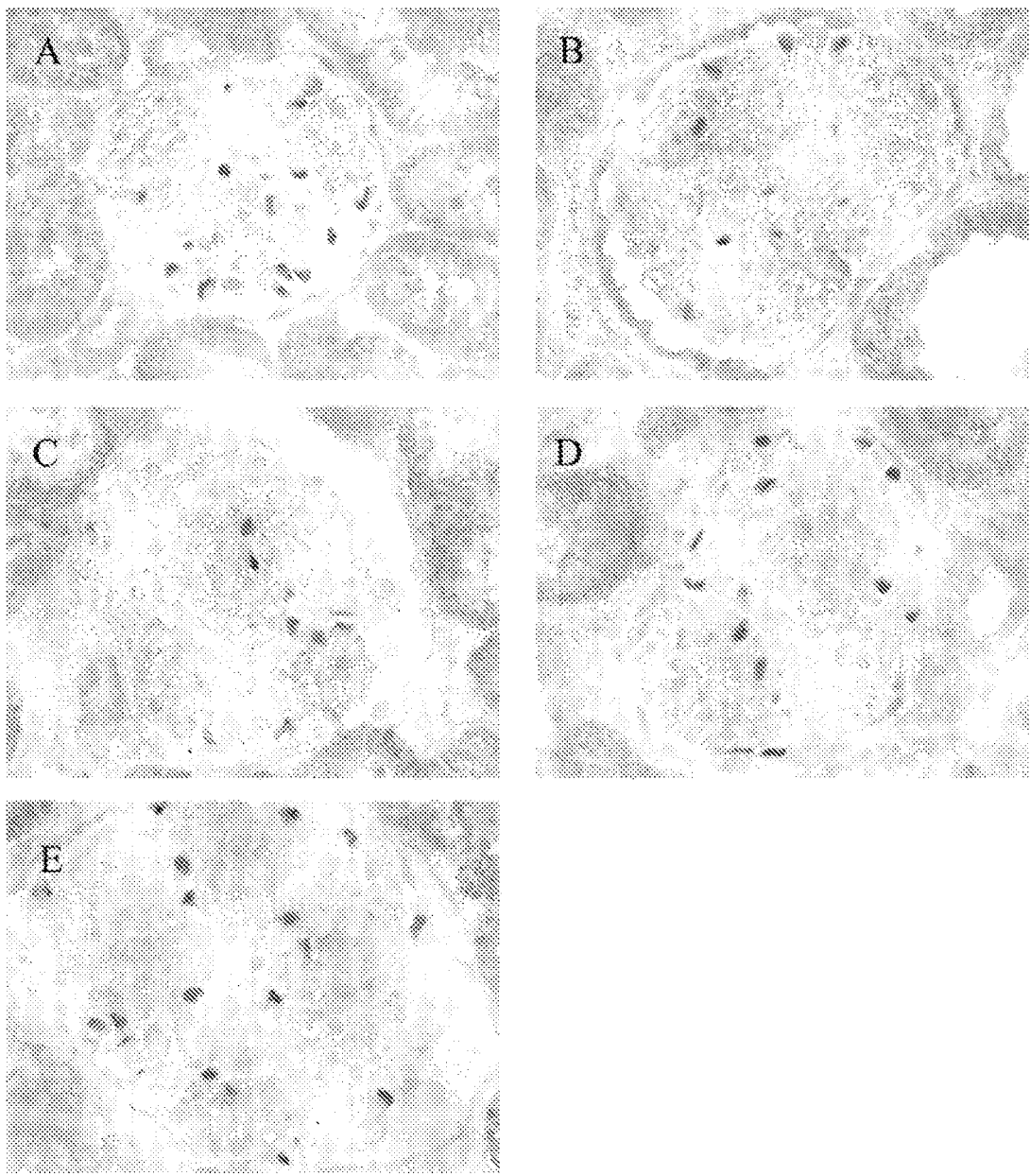
FIG. 3: shows representative phase-contrast images of histological sections obtained from the sub-total nephrectomy (STNx) model of end organ renal disease described in Example 1 showing renal samples obtained from untreated or control animals (A); STNx only (B); STNx and propagermanium (C); STNx and Irbesartan (D); and STNx and Irbesartan in combination (E). Intense brown stained cells in glomerulus represent podocytes.
Figure 4:
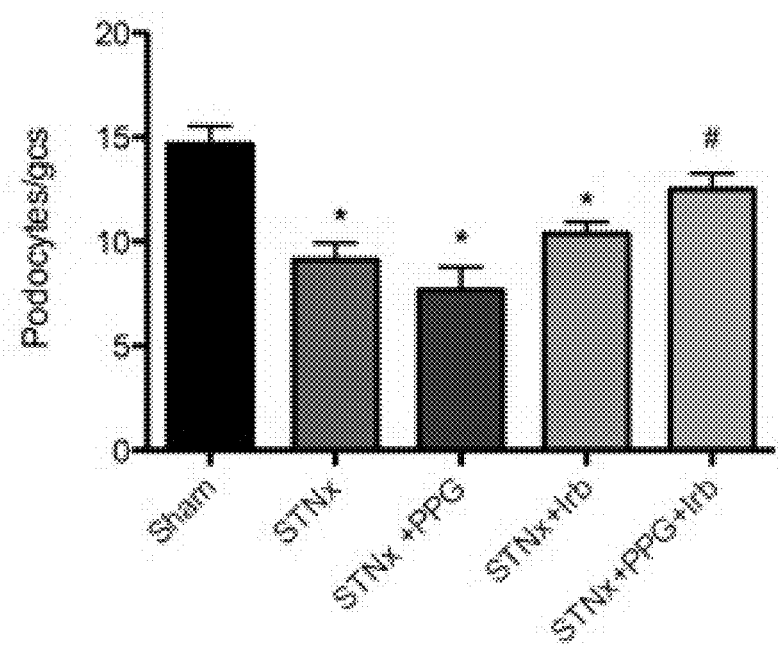
FIG. 4: shows a bar graph of the improvement in numbers of podocytes achieved in the sub-total nephrectomy (STNx) model of end organ renal disease when treated with a combination of Irbesartan (Irb), an angiotensin receptor blocker, and propagermanium (PPG) (a chemokine receptor pathway inhibitor) (high dose) as compared to untreated animals, animals treated with PPG alone, and animals treated with Irbesartan (the angiotensin receptor blocker) alone as described in Example 2.

Histological sections were obtained from the sub-total nephrectomy (STNx) model of end organ renal disease described above and stained according to standard procedures to detect podocytes in the glomerulus. The histological sections were assessed by phase-contrast microscopy. FIG. 3 shows intense brown stained cells (podocytes) in the glomerulus of renal samples obtained from untreated control animals (A); STNx untreated (B); STNx treated with propagermanium (C); STNx treated with Irbesartan (D); and STNx treated with propagermanium and Irbesartan in combination (E). FIG. 4 shows a bar graph of the improvement in numbers of podocytes detected. It can be seen that the level of podocytes in animals treated with a combination of Irbesartan and propagermanium was greater than that of untreated animals subjected to the sub-total nephrectomy (STNx) model of end organ renal disease and STNx animals treated with either propagermanium or Irbesartan alone.

Example 3—Upon Co-Expression of AT1R and CCR2 Via Transient Transfection of HEK293FT Cells, Combined Inhibition of Both Receptors Blocks Arrestin Recruitment to a Greater Extent than Inhibition of Either Receptor Alone The combined effect of CCR2 and AT1R inhibition in vitro was investigated by using RS504393 in combination with Irbesartan.

Figure 5:
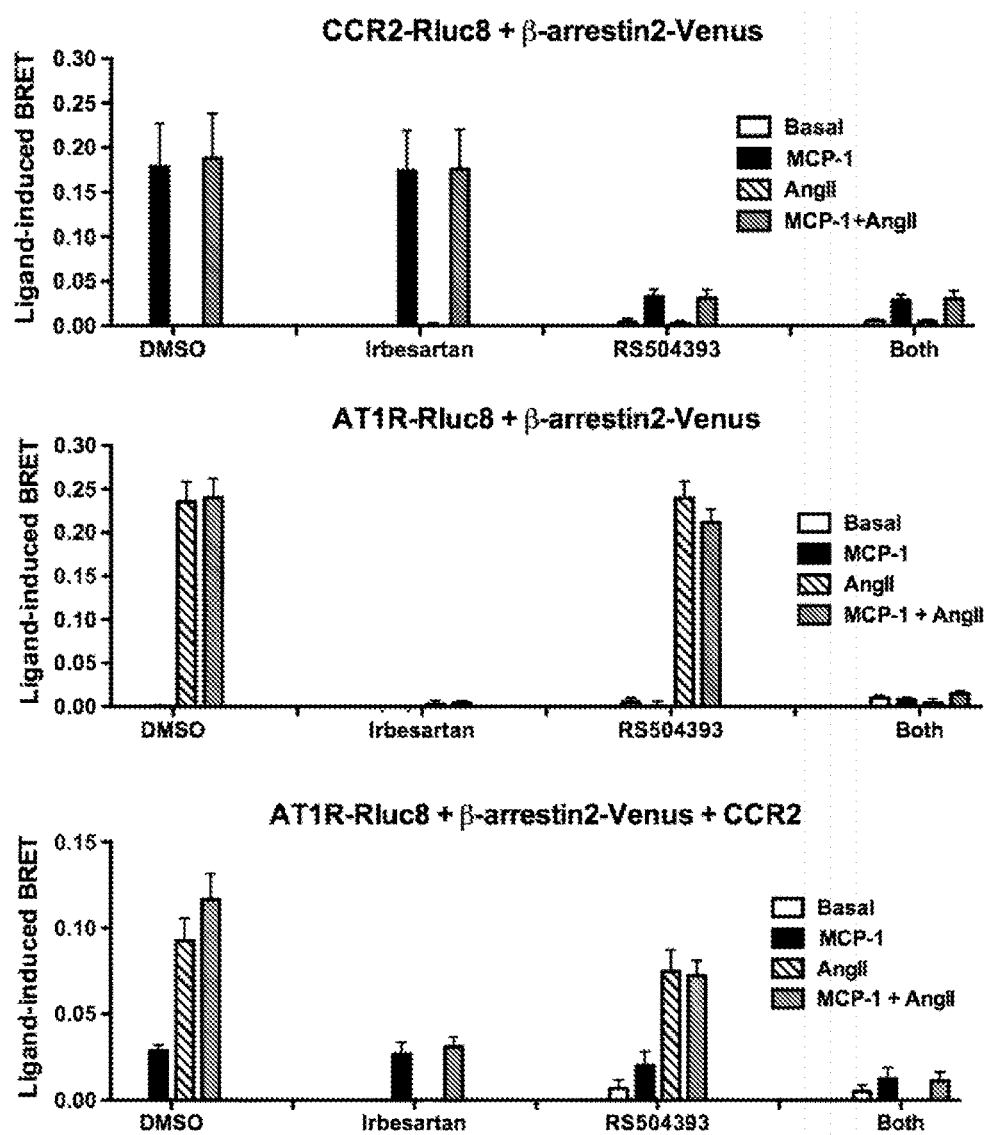
FIG. 5: shows bar graphs indicating the effect of AT1R and CCR2 blockade on β-arrestin2 recruitment as measured by Ligand-induced BRET and described in Example 3. HEK293FT cells were transiently transfected by the plasmids coding for β-arrestin2-Venus and the indicated receptors: CCR2-Rluc8 (top panel), AT1R-Rluc8 (middle panel) or AT1R-Rluc8 and the untagged CCR2 (bottom panel). 48 h post-transfection, cells were used to generate the agonist-induced BRET signal in live cells. For this, cells were first pre-incubated or not for 30 minutes at 37° C. with Irbesartan (10 μM), RS504393 (10 μM) or both combined. Then cells were stimulated or not for 30 minutes at 37° C. with 100 nM of AngII, MCP-1 or both together and the BRET signal was measured. Data represent mean±SEM of three independent experiments performed in triplicate.

FIG. 5 shows the effect of AT1R and CCR2 blockade on β-arrestin2 recruitment. HEK293FT cells were transiently transfected with plasmids coding for β-arrestin2-Venus and the indicated receptors: CCR2-Rluc8 (top panel), AT1R-Rluc8 (middle panel) or AT1R-Rluc8 and the untagged CCR2 (bottom panel).

Cells were harvested 24 h post-transfection in HEPES-buffered phenol red-free complete medium containing 5% FCS and added to a poly-L-lysine-coated white 96-well plate. 48 h post-transfection, the plate was incubated at 37° C., 5% $CO_2$ for 2 hours with 30 µM EnduRen (Promega) to ensure substrate equilibrium was reached.

Cells were first pre-incubated or not for 30 minutes at 37° C. with Irbesartan (10 µM), RS504393 (10 µM) or both combined. Then cells were stimulated or not for 30 minutes at 37° C. with 100 nM of AngII, MCP-1 or both together and the BRET signal was measured.

BRET detection was carried out in live cells by measuring sequential light emissions at 400-475 nm and 520-540 nm before and after agonist addition. The BRET signal was calculated by subtracting the ratio of 520-540 nm emission over 400-475 nm emission for a vehicle-treated cell sample from the same ratio for a second aliquot of the same cells treated with ligand (ligand-induced BRET). Data represent mean±SEM of three independent experiments performed in triplicate.

As shown in FIG. 5 (top panel), 10 µM of RS504393 but not Irbesartan substantially reduced the MCP-1-induced BRET signal between CCR2-Rluc8 and β-arrestin2-Venus. The combination of both antagonists did not substantially alter the inhibitory effect of RS504393 (FIG. 5: top panel). Conversely, in cells co-expressing AT1R-Rluc8 and β-arrestin2-Venus, 10 µM of Irbesartan but not RS504393 substantially blocked the AngII-induced BRET response and their combination did not give any different effect as expected (FIG. 5: middle panel).

However, in cells co-expressing AT1R-Rluc8, β-arrestin2-Venus and untagged CCR2 where both AngII and MCP-1 induced BRET increases to different degrees, Irbesartan seems to substantially block the AngII—but not the MCP-1-induced BRET (FIG. 5: bottom panel). Similarly, RS504393 partially blocked the MCP-1—but not the AngII-promoted BRET signal (FIG. 5: bottom panel). Importantly, the combination of both antagonists reduced the BRET response to levels below that observed with either individual antagonist alone, providing in vitro evidence for a greater inhibition of receptor-mediated cellular response, in this case β-arrestin recruitment, as a consequence of combined receptor inhibition.

Example 4—Upon Co-Expression of AT1R and CCR2 Via Transient Transfection of HEK293FT Cells, Combined Inhibition of Both Receptors Blocks Inositol Phosphate Signalling to a Greater Extent than Inhibition of Either Receptor Alone RS504393 was used in combination with Irbesartan to investigate the combined effect of CCR2 and AT1R inhibition in vitro.

Figure 6:
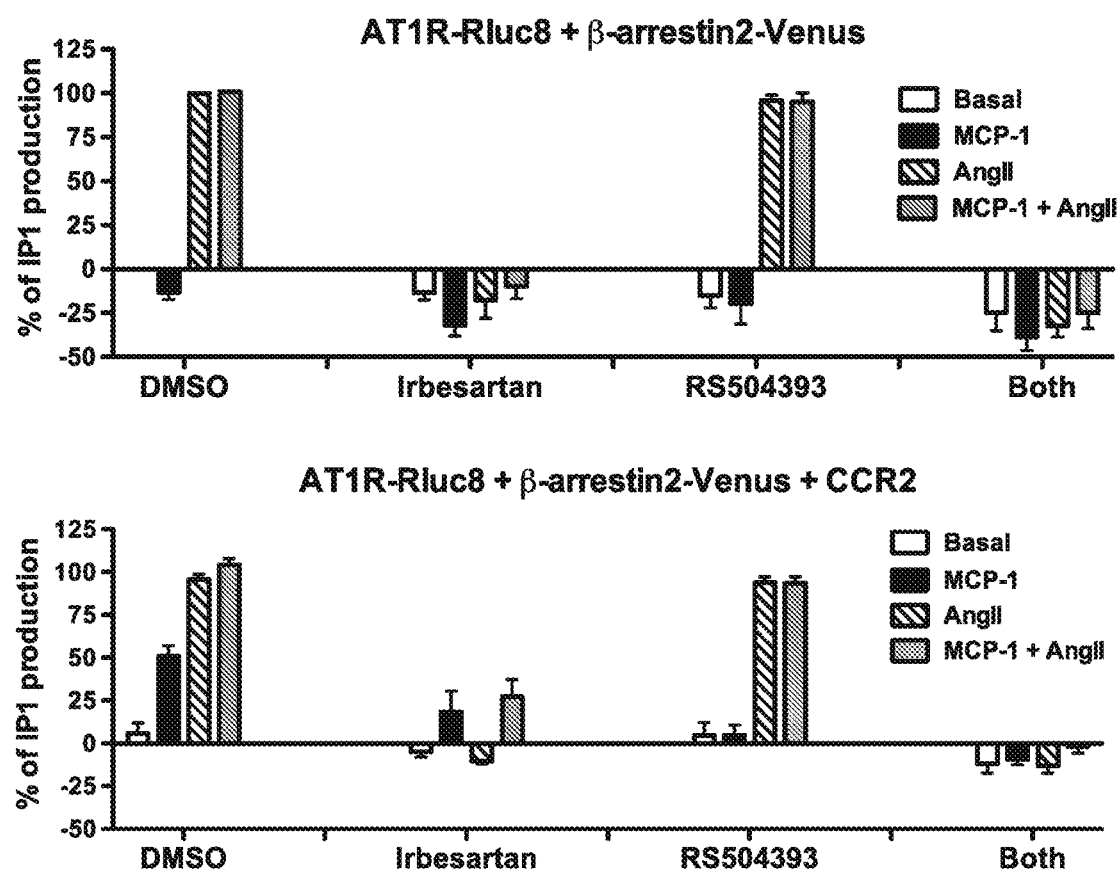
FIG. 6: shows bar graphs indicating effect of AT1R and CCR2 blockade on inositol phosphate production as described in Example 4. HEK293FT cells were transiently transfected with the plasmids coding for AT1R-Rluc8 and β-arrestin2-Venus in the absence (top panel) and presence (bottom panel) of untagged CCR2. 48 h post-transfection, cells were used to generate the agonist-induced inositol (1) phosphate (IP1) production measurements. For this, cells were first pre-incubated or not for 30 minutes at 37° C. with Irbesartan (10 µM), RS504393 (10 µM) or both combined. Then cells were stimulated or not for 30 minutes at 37° C. with 100 nM of AngII, MCP-1 or both together and IP1 production was measured. Data are normalized as a percentage of AngII-induced IP1 production in cells expressing AT1R alone. Data represent mean±SEM of three independent experiments performed in triplicate.

FIG. 6 shows the effect of AT1R and CCR2 blockade on inositol phosphate production. HEK293FT cells were transiently transfected with the plasmids coding for AT1R-Rluc8 and β-arrestin2-Venus in the absence (top panel) and presence (bottom panel) of untagged CCR2. 48 h post-transfection, cells were used to generate the agonist-induced inositol (1) phosphate (IP1) production measurements using the IP-One Tb kit (Cisbio Bioassays, Bagnol sur Ceze, France).

Cells were first pre-incubated or not for 30 minutes at 37° C. with Irbesartan (10 μM), RS504393 (10 μM) or both combined. Cells were then incubated for a further 30 minutes at 37° C. in the stimulation buffer (10 mM HEPES, pH 7.4, 1 mM $CaCl_2$, 0.5 mM $MgCl_2$, 4 mM KCl, 146 mM NaCl, 5.5 mM glucose, and 50 mM LiCl) containing 100 nM of AngII, MCP-1 or both together. The cells were then lysed by adding the HTRF® assay reagents, the Terbium Cryptate-labeled anti-IP1 antibody, and the d2-labeled IP1 analog, previously diluted in the lysis buffer containing 1% Triton X-100. The assay was incubated for 1 hour at room temperature, and Terbium Cryptate fluorescence and the time resolved FRET signal were measured 50 ρs after excitation at 340, 620, and 665 nm, respectively, using the EnVision 2102 multilabel plate reader (PerkinElmer).

Data are normalized as a percentage of AngII-induced IP1 production in cells expressing AT1R alone. Data represent mean±SEM of three independent experiments performed in triplicate.

As shown in FIG. 6 (top panel), 10 μM of Irbesartan, but not RS504393, substantially abolished the AngII-induced IP1 production in cells expressing AT1R-Rluc8. The Irbesartan effect was not substantially altered by its combination with RS504393 in the absence of CCR2 co-expression, demonstrating the specificity of the antagonist.

In cells co-expressing both AT1R-Rluc8 and CCR2, in addition to AngII-mediated IP1 response, MCP-1 also seems to stimulate a partial IP1 response (FIG. 6: bottom panel). Interestingly, Irbesartan partially reduced MCP-1-induced IP1 production, as well as substantially inhibiting the response induced by AngII (FIG. 6: bottom panel). In contrast, RS504393 had little effect on AngII-induced IP1 production, but substantially and selectively inhibited MCP-1-induced IP1 response (FIG. 6: bottom panel). More interestingly, the combination of both antagonists substantially abolished the IP1 production promoted by both MCP-1 and AngII as the two receptors are simultaneously inhibited (FIG. 6: bottom panel). Together, these data clearly indicate the specificity of the MCP-1-dependent IP1 response via CCR2 and imply that the activation of both AT1R and CCR2 are required for such a response. Moreover, these findings provide further in vitro evidence for a greater inhibition of receptor-mediated cellular response, in this case inositol phosphate production, as a consequence of combined receptor inhibition.

Example 5—Upon Co-Expression of AT1R and CCR2 Via Transient Transfection of HEK293FT Cells, Combined Inhibition of Both Receptors Blocks Arrestin Recruitment to a Greater Extent than Inhibition of Either Receptor Alone, as Observed Using the Opposite Orientation of Tagged Versus Untagged Receptor and Using Either of Two Different AngII Antagonists The combined effect of CCR2 and AT1R inhibition in vitro was investigated by using RS504393 in combination with Irbesartan or EXP3174, the active metabolite of Losartan.

Figure 7:
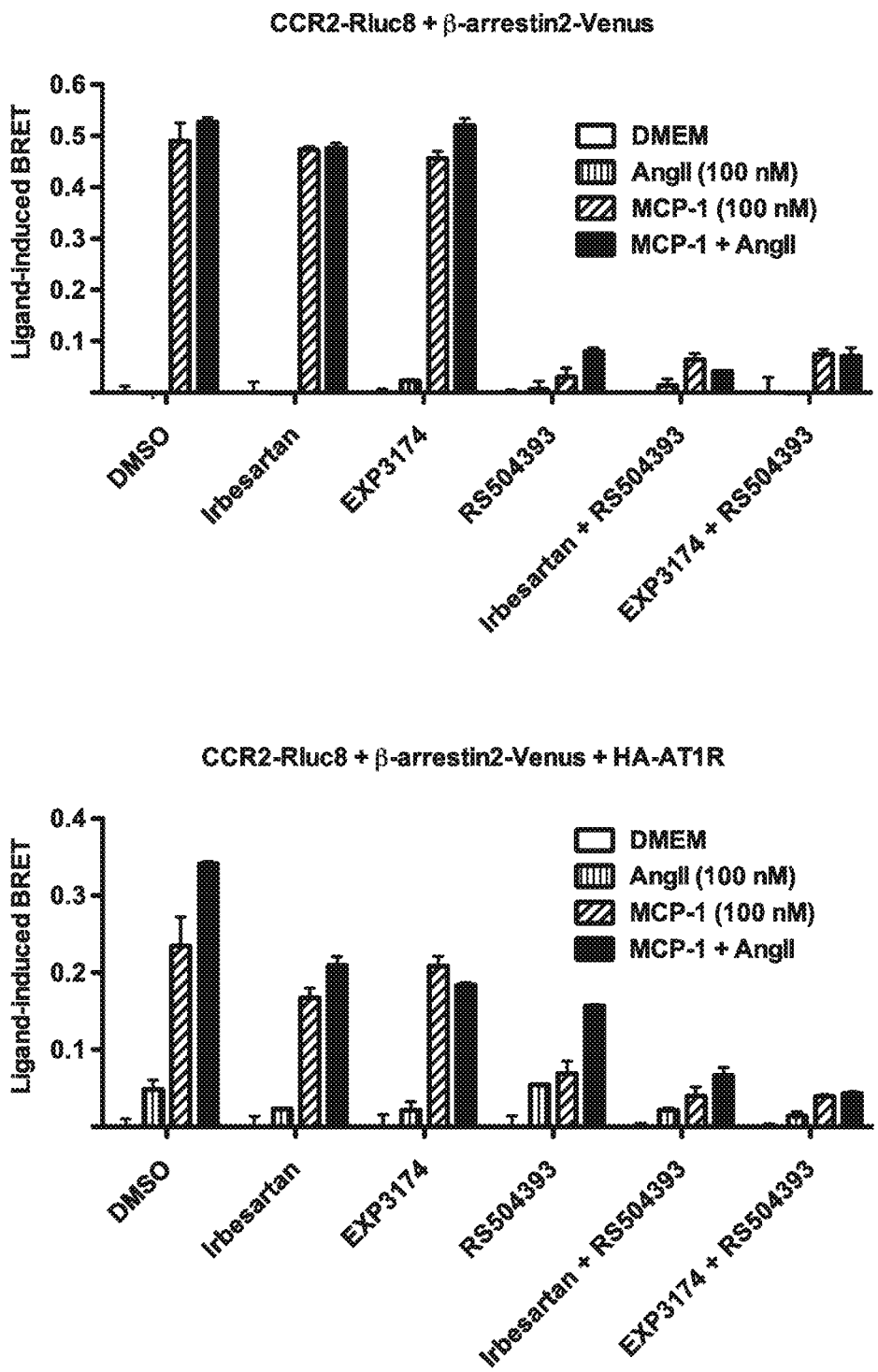
FIG. 7: shows bar graphs indicating the effect of AT1R and CCR2 blockade on β-arrestin2 recruitment as measured by Ligand-induced BRET and described in Example 5. HEK293FT cells were transiently transfected by the plasmids coding for CCR2-Rluc8 and β-arrestin2-Venus in the absence (top panel) and presence (bottom panel) of haemagglutinin (HA)-tagged AT1R. 48 h post-transfection, cells were used to generate the agonist-induced BRET signal in live cells. For this, cells were first pre-incubated or not for 30 minutes at 37° C. with Irbesartan (10 µM), EXP3174 (the active metabolite of Losartan; 10 µM), RS504393 (10 µM) or combinations of Irbesartan and RS504393 or EXP3174 and RS504393. Then cells were stimulated or not for 30 minutes at 37° C. with 100 nM of AngII, MCP-1 or both together and the BRET signal was measured.

FIG. 7 shows the effect of AT1R and CCR2 blockade on β-arrestin2 recruitment. HEK293FT cells were transiently transfected by the plasmids coding for CCR2-Rluc8 and β-arrestin2-Venus in the absence (top panel) and presence (bottom panel) of haemagglutinin (HA)-tagged AT1R.

Cells were harvested 24 h post-transfection in HEPES-buffered phenol red-free complete medium containing 5% FCS and added to a poly-L-lysine-coated white 96-well plate. 48 h post-transfection, the plate was incubated at 37° C., 5% $CO_2$ for 2 hours with 30 μM EnduRen (Promega) to ensure substrate equilibrium was reached.

Cells were first pre-incubated or not for 30 minutes at 37° C. with Irbesartan (10 μM), EXP3174 (the active metabolite of Losartan; 10 μM), RS504393 (10 μM) or combinations of Irbesartan and RS504393 or EXP3174 and RS504393. Then cells were stimulated or not for 30 minutes at 37° C. with 100 nM of AngII, MCP-1 or both together and the BRET signal was measured.

BRET detection was carried out in live cells by measuring sequential light emissions at 400-475 nm and 520-540 nm before and after agonist addition. The BRET signal was calculated by subtracting the ratio of 520-540 nm emission over 400-475 nm emission for a vehicle-treated cell sample from the same ratio for a second aliquot of the same cells treated with ligand (ligand-induced BRET).

As shown in FIG. 7 (top panel), in cells co-expressing CCR2-Rluc8 and β-arrestin2-Venus, 100 nM of AngII had no effect. 10 μM of RS504393, but neither Irbesartan nor EXP3174, substantially blocked the MCP-1-induced BRET response and their combination did not give any different effect as expected (FIG. 7: top panel).

However, in cells co-expressing CCR2-Rluc8, β-arrestin2-Venus and HA-tagged AT1R where both AngII and MCP-1 induced BRET increases to different degrees, RS504393 substantially inhibited the MCP-1-induced but not the AngII-induced BRET (FIG. 7: bottom panel). Similarly, Irbesartan or EXP3174 partially blocked the AngII— but not the MCP-1-promoted BRET signal (FIG. 7: bottom panel). Notably however, with combined treatment with MCP-1 and AngII, a substantial BRET signal remained despite treatment with RS504393. Importantly, the combination of Irbesartan or EXP3174 with RS504393 reduced the BRET response to levels below that observed with either individual antagonist alone, providing in vitro evidence for a greater inhibition of receptor-mediated cellular response, in this case β-arrestin recruitment, as a consequence of combined receptor inhibition.

Example 6—Upon Co-Expression of AT1R and CCR2 Via Transient Transfection of HEK293FT Cells, Combined Inhibition of Both Receptors Blocks Inositol Phosphate Signalling to a Greater Extent than Inhibition of Either Receptor Alone, as Demonstrated with Another AngII Antagonist, EXP3174, the Active Metabolite of Losartan RS504393 was used in combination with EXP3174 to investigate the combined effect of CCR2 and AT1R inhibition in vitro.

Figure 8:
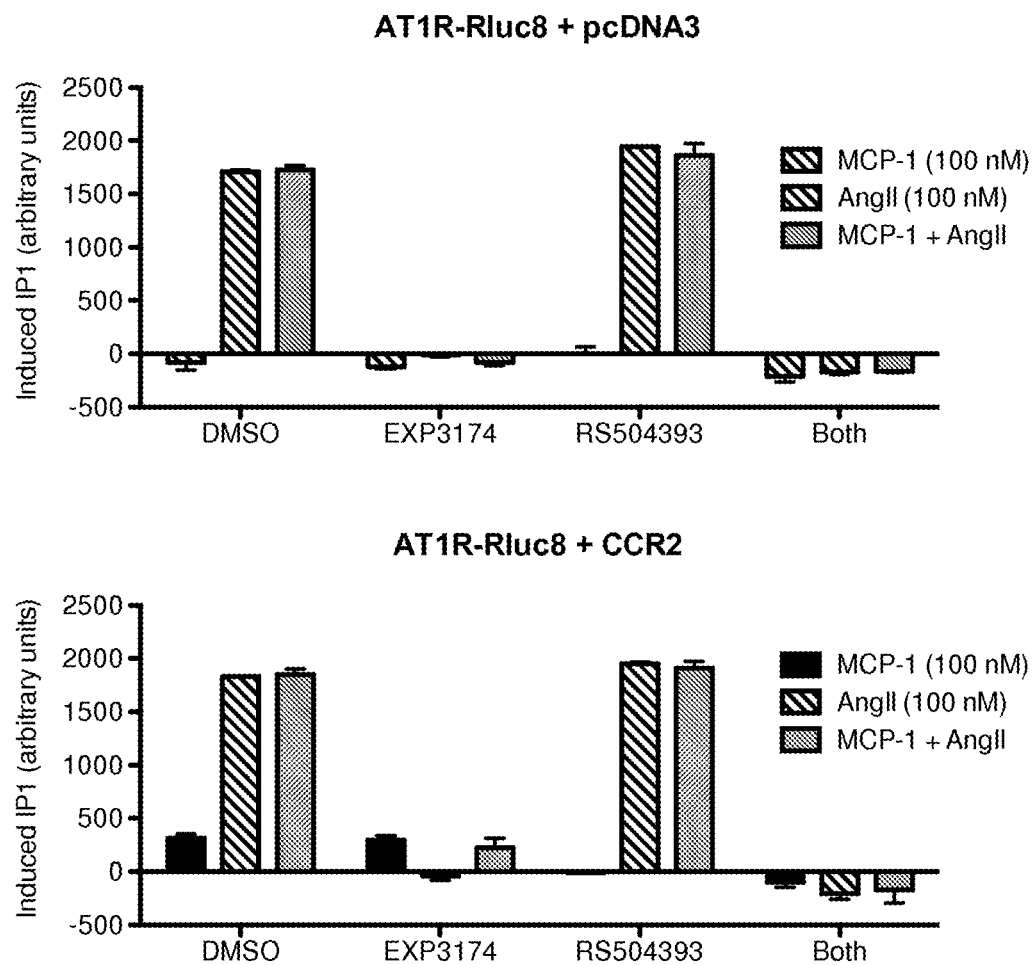
FIG. 8: shows bar graphs indicating effect of AT1R and CCR2 blockade on inositol phosphate production as described in Example 6. HEK293FT cells were transiently transfected with the plasmids coding for AT1R-Rluc8 and β-arrestin2-Venus in the absence (top panel) and presence (bottom panel) of untagged CCR2. 48 h post-transfection, cells were used to generate the agonist-induced inositol (1) phosphate (IP1) production measurements. For this, cells were first pre-incubated or not for 30 minutes at 37° C. with EXP3174 (the active metabolite of Losartan; 10 µM), RS504393 (10 µM) or both combined. Then cells were stimulated or not for 30 minutes at 37° C. with 100 nM of AngII, MCP-1 or both together and IP1 production was measured. Data are shown as induced IP1 (arbitrary units).

FIG. 8 shows the effect of AT1R and CCR2 blockade on inositol phosphate production. HEK293FT cells were transiently transfected with the plasmids coding for AT1R-Rluc8 and β-arrestin2-Venus in the absence (top panel) and presence (bottom panel) of untagged CCR2. 48 h post-transfection, cells were used to generate the agonist-induced inositol (1) phosphate (IP1) production measurements using the IP-One Tb kit (Cisbio Bioassays, Bagnol sur Ceze, France).

Cells were first pre-incubated or not for 30 minutes at 37° C. with EXP3174 (10 µM), RS504393 (10 µM) or both combined. Cells were then incubated for a further 30 minutes at 37° C. in the stimulation buffer (10 mM HEPES, pH 7.4, 1 mM $CaCl_2$, 0.5 mM $MgCl_2$, 4 mM KCl, 146 mM NaCl, 5.5 mM glucose, and 50 mM LiCl) containing 100 nM of AngII, MCP-1 or both together. The cells were then lysed by adding the HTRF® assay reagents, the Terbium Cryptate-labeled anti-IP1 antibody, and the d2-labeled IP1 analog, previously diluted in the lysis buffer containing 1% Triton X-100. The assay was incubated for 1 hour at room temperature, and Terbium Cryptate fluorescence and the time resolved FRET signal were measured 50 ρs after excitation at 340, 620, and 665 nm, respectively, using the EnVision 2102 multilabel plate reader (PerkinElmer). Data are shown as induced IP1 (arbitrary units). The IP-One Tb kit is a competition assay and so induction of IP1 results in a decrease in absolute assay signal. Therefore, the induced IP1 (arbitrary units) is generated by subtracting the ligand-induced assay signal from the basal assay signal.

As shown in FIG. 8 (top panel), 10 µM of EXP3174, but not RS504393, abolished the AngII-induced IP1 production in cells expressing AT1R-Rluc8. The EXP3174 effect was not substantially altered by its combination with RS504393 in the absence of CCR2 co-expression, demonstrating the specificity of the antagonist.

In cells co-expressing both AT1R-Rluc8 and CCR2, in addition to AngII-mediated IP1 response, MCP-1 also seems to stimulate a partial IP1 response (FIG. 8: bottom panel). EXP3174 substantially inhibited the response induced by AngIII (FIG. 8: bottom panel). In contrast, RS504393 had little effect on AngII-induced IP1 production, but substantially and selectively inhibited MCP-1-induced IP1 response (FIG. 8: bottom panel). More interestingly, the combination of both antagonists substantially abolished the IP1 production promoted by both MCP-1 and AngII as the two receptors are simultaneously inhibited (FIG. 8: bottom panel). These findings provide further in vitro evidence for a greater inhibition of receptor-mediated cellular response, in this case inositol phosphate production, as a consequence of combined receptor inhibition.

Figure 9:
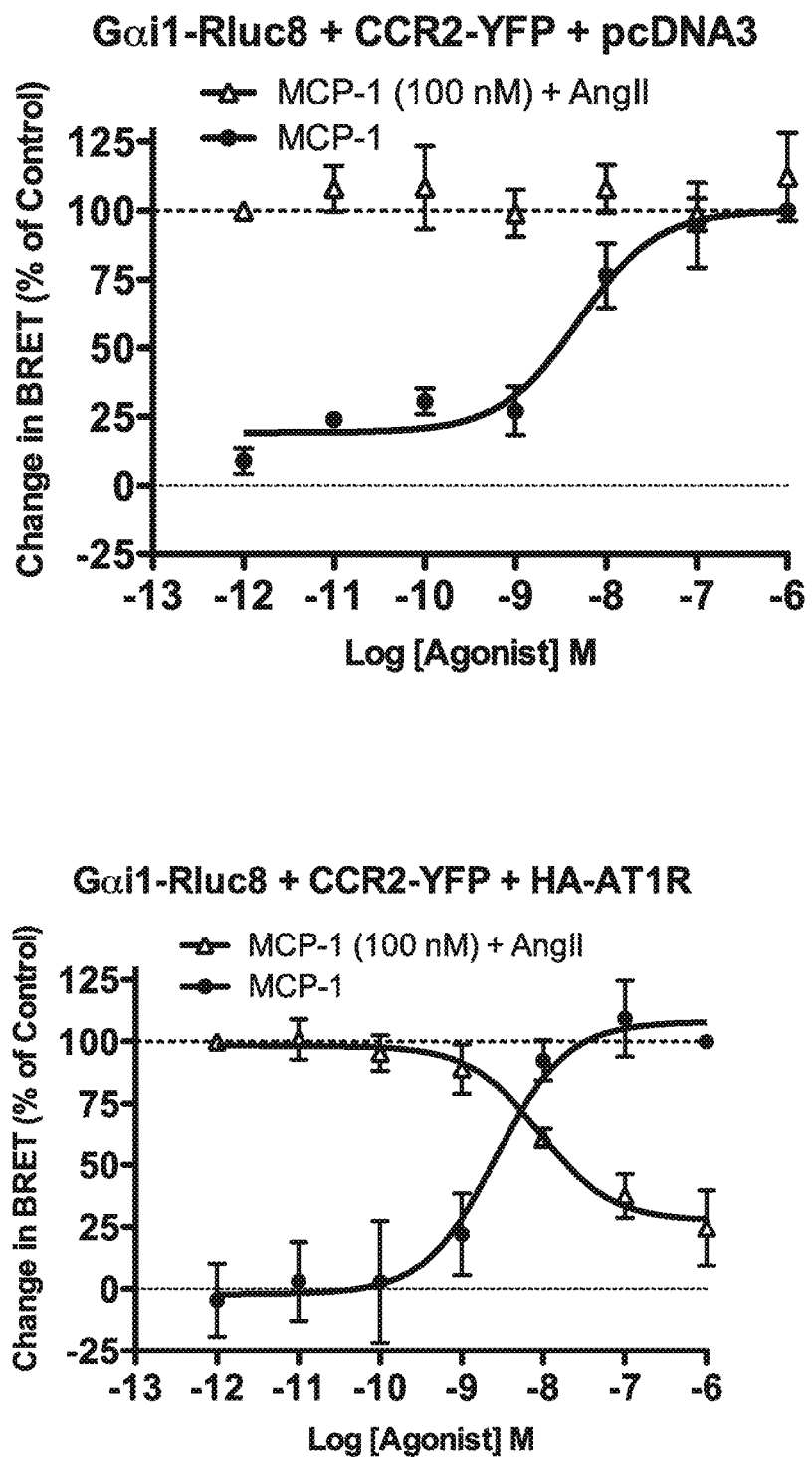
FIG. 9: shows dose-response curves indicating the effect of activating CCR2 in the absence and presence of activated AT1R in terms of $G\alpha_{i1}$ coupling as measured by Ligand-induced BRET and described in Example 7. HEK293FT cells were transiently transfected by the plasmids coding for Gαi1-Rluc8 and CCR2-YFP in the absence (top panel) and presence (bottom panel) of haemagglutinin (HA)-tagged AT1R. 48 h post-transfection, cells were used to generate the agonist-induced BRET signal data in live cells at various concentrations of MCP-1 or at various concentrations of AngII in the presence of 100 nM MCP-1.

Example 7—Specific Activation of the AT1R Inhibits MCP-1-Mediated Coupling to $G\alpha i1$ in a Dose-Dependent Manner, Providing In Vitro Evidence for AT1R Modulating CCR2 Function and Providing Further Rationale for Inhibition of CCR2 in Addition to AngII FIG. 9 shows dose-response curves indicating the effect of activating CCR2 in the absence and presence of activated AT1R in terms of $G\alpha i1$ coupling as measured by Ligand-induced BRET. HEK293FT cells were transiently transfected by the plasmids coding for $G\alpha_{i1}$-Rluc8 and CCR2-YFP in the absence (top panel) and presence (bottom panel) of haemagglutinin (HA)-tagged AT1R. 48 h post-transfection, cells were used to generate the agonist-induced BRET signal data in live cells at various concentrations of MCP-1 or at various concentrations of AngII in the presence of 100 nM MCP-1.

Upon addition of BRET substrate, BRET detection was carried out in live cells by measuring sequential light emissions at 400-475 nm and 520-540 nm before and after agonist addition. The BRET signal was calculated by subtracting the ratio of 520-540 nm emission over 400-475 nm emission for a vehicle-treated cell sample from the same ratio for a second aliquot of the same cells treated with ligand (ligand-induced BRET). Activation of CCR2 resulted in a decrease in BRET ratio, indicating that activation resulted in a change of conformation of a $G\alpha i1$ protein pre-assembled with CCR2, as has been recently described for the PAR1-$G\alpha i1$ interaction (Ayoub M A, Trinquet E, Pfleger K D G and Pin J P (2010) Differential association modes of the thrombin receptor PAR1 with $G\alpha i1$, $G\alpha 12$ and β-arrestin 1. FASEB J 24: 3522-3535). Therefore, the data have been presented as 'Change in BRET (% of Control)' such that the change in BRET signal observed with 1 µM MCP-1 is designated 100%, and no change in BRET signal being designated 0%.

MCP-1 alters the distance and/or orientation between Rluc8 and YFP fused to $G\alpha i1$ and CCR2 respectively in a dose-dependent manner indicative of receptor activation and coupling to $G\alpha i1$-mediated signalling. In the absence of AT1R co-expression, increasing doses of AngII does not alter the MCP-1-induced change in BRET signal observed (FIG. 9: top panel). In contrast, when AT1R is co-expressed, AngII inhibits the MCP-1-induced change in BRET signal in a dose-dependent manner (FIG. 9: bottom panel).

This example provides evidence for AngII inhibiting the MCP-1-induced activation of $G\alpha i1$ coupling by CCR2. Therefore, blockade of AngII alone using an AngII antagonist, would be expected to remove this inhibition of MCP-1-induced $G\alpha i1$ signalling. Treatment with a CCR2 pathway inhibitor in combination with an AngII antagonist would be expected to prevent activation of CCR2-mediated $G\alpha i1$ being exacerbated by AT1R blockade.

Therefore this example provides further in vitro evidence supporting the rationale for using a combination of CCR2 pathway inhibitor and AT1R antagonist.

The claims defining the invention are as follows:

1. A method for the treatment or amelioration of a condition or disease comprising:
    administering to a subject a therapeutically effective amount of a pharmaceutical composition comprising: a) at least one angiotensin 1 receptor blocker (AT1R) or a pharmaceutically acceptable salt thereof, and b) at least one chemokine receptor 2 (CCR2) inhibitor or a pharmaceutically acceptable salt thereof selected from the group consisting of direct CCR2 antagonists, inverse CCR2 agonists, negative allosteric CCR2 modulators, indirect CCR2 antagonists, indirect inverse CCR2 agonists, and indirect allosteric CCR2 modulators,
    wherein the condition or disease is a monocyte chemoattractant protein 1 (an MCP-1) mediated or a CCR2 mediated condition or disease and wherein the MCP-1 mediated or a CCR2 mediated condition is a kidney disease selected from the group consisting of fibrotic disorders in the kidney, chronic kidney disease caused by diabetic nephropathy, renal insufficiency, renal failure conditions, diabetic nephropathy, glomerulonephritis, glomerular sclerosis, and proteinuria of primary renal disease.

2. The method of treatment or amelioration of claim 1, wherein:
    a) when the CCR2 inhibitor is administered to a subject concurrently or sequentially with an AT1R blocker, the combined affinity, potency and/or efficacy is greater than compared to the affinity, potency and/or efficacy that would have been achieved when the CCR2 inhibitor is not administered in combination with the AT1R blocker; and/or
    b) when the AT1R blocker is administered to a subject concurrently or sequentially with a CCR2 inhibitor, the combined affinity, potency and/or efficacy is greater than compared to the affinity, potency and/or efficacy that would have been achieved when the AT1R blocker is not administered in combination with the CCR2 inhibitor.

3. The method of treatment or amelioration of claim 1, wherein the CCR2 inhibitor is selected from the group consisting of: propagermanium; RS504393; RS102895; MLN-1202; INCB8696; MK-0812; CCX140; PF-4136309; and BMS-741672.

4. A method of treating kidney disease in a subject in need thereof, said method comprising administering to the subject a therapeutically effective amount of a CCR2 inhibitor concurrently or sequentially with an AT1R blocker, wherein the kidney disease is selected from the group consisting of fibrotic disorders in the kidney, chronic kidney disease caused by diabetic nephropathy, renal insufficiency, renal failure conditions, diabetic nephropathy, glomerulonephritis, glomerular sclerosis, and proteinuria of primary renal disease.

5. The method of claim 4, wherein the subject is concurrently receiving AT1R blocker therapy when the CCR2 inhibitor is administered.

6. The method of claim 4, wherein the subject is administered the AT1R blocker therapy in a different dosage unit than the CCR2 inhibitor.

7. The method of treatment or amelioration of claim 1, wherein the CCR2 inhibitor:
   a) inhibits or partially inhibits CCR2; and/or
   b) is selected from the group consisting of: propagermanium; RS504393; MLN-1202; 1NCB8696; MK-0812; CCX140; PF-4136309; RS102895; and BMS-741672.

8. The method of treatment or amelioration of claim 1, wherein the CCR2 inhibitor stabilizes the complexes CCR2/CD55, CCR2/CD59 and/or CCR2/CD16.

9. The method of treatment or amelioration of claim 1, wherein:
   a) the AT1R blocker inhibits or partially inhibits the activation of AT1R;
   b) the AT1R blocker is selected from the group consisting of:
      (i) an AT1R antagonist;
      (ii) an inverse AT1R agonist; and
      (iii) a negative allosteric AT1R modulator; and/or
   c) the AT1R blocker is selected from the group consisting of: eprosartan; losartan; valsartan; telmisartan; candesartan; and ZD-7115.

10. The method of treatment or amelioration of claim 1, wherein the CCR2 inhibitor inhibits MCP-1 induced migration and activation of monocytes and chemotactic migration through the targeting of one or more glycosylphosphatidylinositol (GPI)-anchored proteins selected from the group consisting of CD55, CD59 and CD16.

11. The method of treatment or amelioration of claim 1, wherein the composition comprises about 5 mg to 1 g of the AT1R blocker or a pharmaceutically acceptable salt thereof, and about 5 mg to 1 g of the CCR2 inhibitor or a pharmaceutically acceptable salt thereof.

12. The method of treatment or amelioration of claim 1, wherein the composition comprises a combination of:
   a) a CCR2 inhibitor selected from the group consisting of: propagermanium; RS504393; MLN-1202; INCB8696; MK-0812; CCX140; PF-4136309; RS102895; and BMS-741672; and
   b) an AT1R blocker selected from the group consisting of: eprosartan; losartan; valsartan; telmisartan; candesartan; and ZD-7115.

13. The method of treatment or amelioration of claim 1, wherein the CCR2 inhibitor is RS504393 or propagermanium.

14. The method of treatment or amelioration of claim 1, comprising:
   a) at least one AT1R blocker or a pharmaceutically acceptable salt thereof; and
   b) at least one CCR2 inhibitor or a pharmaceutically acceptable salt thereof which inhibits a component of the CCR2 pathway other than CCR2.

15. The method of treatment or amelioration of claim 14, wherein the CCR2 inhibitor inhibits MCP-1 induced migration and activation of monocytes and chemotactic migration through the targeting of one or more glycosylphosphatidylinositol (GPI)-anchored proteins selected from the group consisting of CD55, CD59 and CD16.

16. The method of treatment or amelioration of claim 14, wherein the CCR2 inhibitor stabilizes the complexes CCR2/CD55, CCR2/CD59 and/or CCR2/CD16.

17. The method of treatment or amelioration of claim 14, wherein:
   a) the AT1R blocker inhibits or partially inhibits the activation of AT1R;
   b) the AT1R blocker is selected from the group consisting of:
      (i) an AT1R antagonist;
      (ii) an inverse AT1R agonist; and
      (iii) a negative allosteric AT1R modulator; and/or
   c) the AT1R blocker is selected from the group consisting of: eprosartan; losartan; valsartan; telmisartan; candesartan; and ZD-7115.

18. The method of claim 3, wherein the CCR2 inhibitor is propagermanium or RS504393.

19. The method of claim 1, wherein the AT1R blocker is not olmesartan.

20. The method of claim 1, wherein the CCR2 inhibitor is not RS102895.

21. The method of claim 1, wherein the AT1R blocker is not olmesartan and the CCR2 inhibitor is not RS102895.

22. The method of claim 1, wherein the CCR2 inhibitor is propagermanium and the AT1R blocker is olmesartan or irbesartan.

* * * * *